United States Patent
Harmon et al.

(10) Patent No.: US 11,999,805 B1
(45) Date of Patent: Jun. 4, 2024

(54) PEPTIDE INHIBITORS OF CRISPR-CAS9

(71) Applicant: National Technology & Engineering Solutions of Sandia, LLC, Albuquerque, NM (US)

(72) Inventors: Brooke Nicole Harmon, Livermore, CA (US); Yooli Kim Light, Pleasanton, CA (US); Mary Bao Tran-Gyamfi, Pleasanton, CA (US); Joseph S. Schoeniger, Oakland, CA (US); Edwin A. Saada, Dublin, CA (US); Kenneth L. Sale, Pleasanton, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 124 days.

(21) Appl. No.: 16/867,698

(22) Filed: May 6, 2020

(51) Int. Cl.
  *C07K 7/08* (2006.01)
  *A61K 38/46* (2006.01)
  *C07K 14/00* (2006.01)
  *A61K 9/00* (2006.01)

(52) U.S. Cl.
  CPC ............. *C07K 7/08* (2013.01); *A61K 38/465* (2013.01); *C07K 14/001* (2013.01); *A61K 9/0053* (2013.01); *C12N 2310/20* (2017.05); *C12N 2310/3513* (2013.01); *C12N 2310/3519* (2013.01); *C12Y 301/00* (2013.01)

(58) Field of Classification Search
  None
  See application file for complete search history.

(56) References Cited

U.S. PATENT DOCUMENTS

2019/0030190 A1* 1/2019 Peyman ................. C12N 15/87

FOREIGN PATENT DOCUMENTS

WO WO2018197520 * 11/2018

OTHER PUBLICATIONS

Bondy-Denomy J ('Protein inhibitors of CRISPR-Cas9' ACS Chem Biol v13 2018 pp. 417-423) (Year: 2018).*
NCBI entry (retrieved from https://www.ncbi.nlm.nih.gov/protein/WP_003723290.1 on Mar. 16, 2022, 1 page) (Year: 2022).*
Sequence listing entry 647 for WO 2018/197520 dated Nov. 2018 (retrieved from https://patentscope.wipo.int/search/en/detail.jsf?docId=WO2018197520 on Mar. 16, 2022, 1 page) (Year: 2018).*
Seamon, et al., "Versatile High-Throughput Fluorescence Assay for Monitoring Cas9 Activity", in Analytical Chemistry, American Chemical Society, vol. 90, 2018, pp. 6913-6921.
Di, L., "Strategic Approaches to Optimizing Peptide ADME Properties", in the AAPS Journal, American Association of Pharmaceutical Sciences, vol. 17, No. 1, Jan. 2015, pp. 134-143.
Mishra, et al., "Low Cationicity is Important for Systemic in Vivo Efficacy of Database-Derived Peptides Against Drug-Resistant Gram-Positive Pathogens", in PNAS, vol. 116, No. 27, Jul. 2, 2019, pp. 13517-13522.
Walensky, et al., "Activation of Apoptosis in Vivo by a Hydrocarbon-Stapled BH3 Helix", in Science, NIH Public Access, vol. 305, No. 5689, Sep. 3, 2004, pp. 1466-1470.

* cited by examiner

*Primary Examiner* — Ronald T Niebauer
(74) *Attorney, Agent, or Firm* — Eschweiler & Potashnik, LLC; Madelynne Farber; Samantha Updegraff

(57) ABSTRACT

Specific and broad-spectrum inhibitory peptides to CRISPR Cas9 variants (SpyCas9, SauCas9, and CjeCas9) are disclosed. A method of making and using these peptides with therapeutic CRISPR Cas9 (to improve desired targeting) or against harmful CRISPR Cas9 components (already active in a patient) is also disclosed. The peptides combined with a delivery system is also disclosed.

18 Claims, 13 Drawing Sheets

Specification includes a Sequence Listing.

Initial screening with FRET based high-throughput assay

Secondary screening of peptide inhibition by cleaved substrate on denatured gel (15% urea PAGE)

Binding Inhibition Assay of Peptides (200 uM) Against SpyCas9

PEPTIDE INHIBITORS OF CRISPR-CAS9

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD15067_SL.txt," created on Apr. 27, 2020 (size of 11 kilobytes), which is hereby incorporated by reference in its entirety.

FIELD

This disclosure relates to peptides that inhibit Cas9 variants.

BACKGROUND

CRISPR (clustered, regularly interspaced, short 37 palindromic repeats)/Cas9 is a bacterial derived gene editing system. While it has been repurposed to edit specifically targeted sequences, it can also be a pathogenic threat.

The application of CRISPR-Cas9 as a "programmable" genetic editing technique allows easy and precise editing of the genome of any organism, with much greater ease than was previously possible, but the use of CRISPR/Cas9 for therapeutic editing of the genome carries risks, such as off-target editing. The use of Cas9 inhibitors for dose and spatial-temporal control of Cas9 activity would greatly enhance the safety and efficacy of CRISPR-based gene therapies and provide an antidote in the event of unwanted exposure.

Discovery of small molecule inhibitors of Cas9 is challenging due to the avidity of Cas9 protein to sgRNA and DNA, the large binding sites for the DNA substrate and the specific conformational changes required for activity. Several natural anti-CRISPR (Acr) proteins with highly effective inhibitory activity against different Cas proteins have been identified, but these proteins are difficult to deliver. In addition, these proteins tend to be specific to one or two species of Cas9, and the large interface required for the tight binding of the Acr to the Cas protein, means that small sequence changes in engineered Cas gene editors may disrupt binding. If identified, small molecules have the benefit of being cell penetrating, more suitable for oral delivery, and easier to manufacture than proteins, but they can produce toxic metabolites, result in off-target binding and tend to be less potent.

SUMMARY

Peptides were synthesized and found to inhibit one or more Cas-9 variants. In an embodiment, multiple Cas9 variants are inhibited by a synthesized peptide. It is believed that this represents the first identification of broad spectrum anti-CRISPR therapeutics. These peptides were identified using a phage display assay to screen an in-house synthesized peptide library of $1\times10^8$ random 22mer peptides displayed on T7-phage for high affinity binding to Cas9.

These peptides can be used as anti-CRISPR agents to improve targeting of CRISPR Cas9 (cancelling out unwanted targets), inactivate CRISPR-Cas9 in certain environments (allowing a latent activation), or to counter a body's reaction to an accidental/erroneous or intentionally harmful CRISPR-Cas9 activity before it has time to fully act on a body.

In an embodiment, an anti-CRISPR bioactive agent is selected from the group consisting of: an amino acid sequence having at least 80% sequence identity to any one of SEQ ID NOs: 1-28 or an analog thereof and combinations thereof.

In an embodiment, a composition comprises an amino acid sequence has at least 80% sequence identity to any one of SEQ ID NOs:1-27 or a fragment thereof, and a pharmaceutically acceptable excipient.

In an embodiment, a method of treatment includes the steps of: administering to a patient in need thereof, an effective amount of a composition comprising an amino acid sequence having at least 80% sequence identity to any one of SEQ ID NOs:1-27 or a fragment thereof; and a pharmaceutically acceptable excipient.

DETAILED DESCRIPTION

Figure 1:
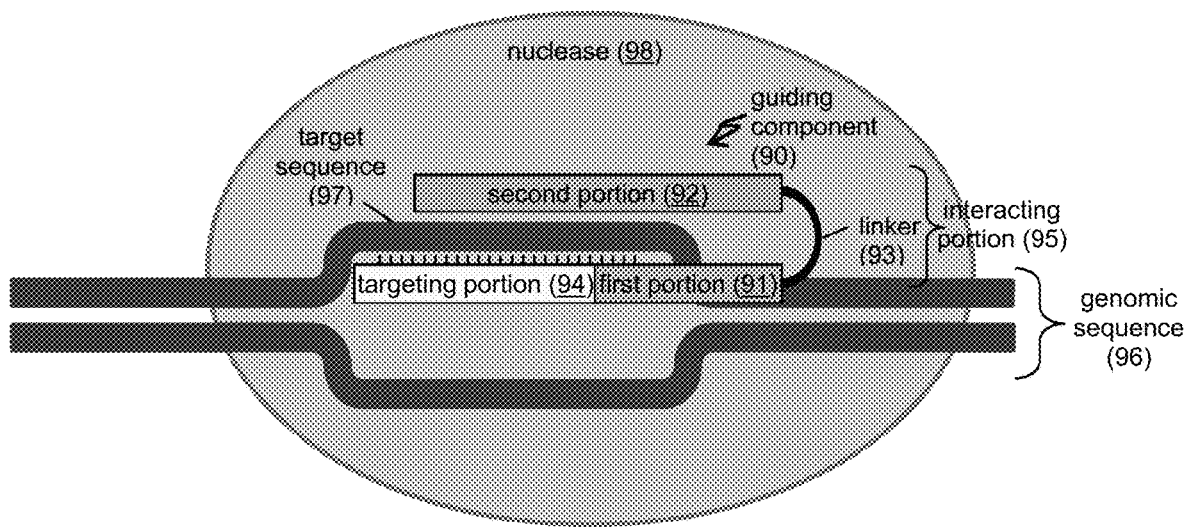
FIG. 1 is a schematic view of an exemplary CRISPR component that includes a guiding component 90 to bind to the target sequence 97, as well as a nuclease 98.

As used herein, the term "about" means+/−10% of any recited value. As used herein, this term modifies any recited value, range of values, or endpoints of one or more ranges.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something and is not intended to indicate a preference.

By "micro" is meant having at least one dimension that is less than 1 mm but equal to or larger than 1 μm. For instance, a microstructure (e.g., any structure described herein, such as a microparticle) can have a length, width, height, cross-sectional dimension, circumference, radius (e.g., external or internal radius), or diameter that is less than 1 mm but equal to or larger than 1 μm. In another instance, the microstructure has a dimension that is of from about 1 μm to 1 mm.

By "nano" is meant having at least one dimension that is less than 1 μm but equal to or larger than 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than 1 nm. In another instance, the nanostructure has a dimension that is of from about 1 nm to about 1 μm.

The term "lipid" is used to describe the components which are used to form lipid mono-, bi-, or multilayers on the surface of the particles (e.g., a core of the particle), that are used in the present disclosure (e.g., as constructs) and may include a PEGylated lipid. Various embodiments provide nanostructures, that are constructed from nanoparticles, which support one or more lipid layers (e.g., bilayer(s) or multilayer(s)).

The term "reporter" is used to describe an imaging agent or moiety that is incorporated into the outer layer or cargo of particles according to an embodiment of the present disclosure and provides a signal that can be measured. The moiety may provide a fluorescent signal or may be a radioisotope which allows radiation detection, among others. Exemplary fluorescent labels for use in particles (e.g., via conjugation or adsorption to the outer layer or the core, via integration into the matrix of the core, and/or via incorporation into cargo elements such as DNA, RNA-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670), Alexa Fluor® 647 conjugate of annexin V (650/665), other fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof etc. Additional reporters can include a detection agent (e.g., a dye, such as an electroactive detection agent, a fluorescent dye, a luminescent dye, a chemiluminescent dye, a colorimetric dye, a radioactive agent, a contrast agent, etc.), a particle (e.g., such as a microparticle, a nanoparticle, a latex bead, a colloidal particle, a magnetic particle, a fluorescent particle, etc.), and/or a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes). Moieties that enhance the fluorescent signal or slow the fluorescent fading may also be incorporated and include SlowFade® Gold antifade reagent (with and without DAPI) and Image-iT® FX signal enhancer. All of these are well known in the art.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the disclosure. In certain embodiments, a polypeptide to be utilized in accordance with the disclosure includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the disclosure.

As used herein, when a peptide sequence is referred to as having "at least X % sequence identity" to a reference sequence, it is meant that at least X percent of the amino acids in the peptide are identical to those of the reference sequence when the sequences are optimally aligned. In general, for peptides, the length of comparison sequences can be at least five amino acids, preferably 10, 20, 30, 40, up to the entire length of the peptide.

By "cleavage" it is meant the breakage of the covalent backbone of a target sequence (e.g., a nucleic acid molecule). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guiding component and a nuclease is used for targeted double-stranded DNA cleavage. In other embodiments, a complex comprising a guiding component and a nuclease is used for targeted single-stranded RNA cleavage.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

By an "effective amount" or a "sufficient amount" of an agent (e.g., a cargo), as used herein, is that amount sufficient to effect beneficial or desired results, such as clinical results, and, as such, an "effective amount" depends upon the context in which it is being applied. For example, in the context of administering an agent that employs a CRISPR component to genetically modify a gene, an effective amount of an agent is, for example, an amount sufficient to achieve increased or decreased expression of that gene, as compared to the response obtained without administration of the agent.

By "subject" or "patient" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

By "salt" is meant an ionic form of a compound or structure (e.g., any formulas, compounds, or compositions described herein), which includes a cation or anion compound to form an electrically neutral compound or structure. For example, non-toxic salts are described in Berge S M et al., "Pharmaceutical salts," J. Pharm. Sci. 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the disclosed technology or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecyl sulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methyl sulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, and valerate salts. Representative cationic salts include metal salts, such as alkali or alkaline earth salts, e.g., barium, calcium (e.g., calcium edetate), lithium, magnesium, potassium, and sodium; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and pyridinium. Other cationic salts include organic salts, such as chloroprocaine, choline, dibenzylethylenediamine, diethanolamine, ethylenediamine, methylglucamine, and procaine. Exemplary salts include pharmaceutically acceptable salts.

By "pharmaceutically acceptable salt" is meant a salt that is, within the scope of sound medical judgment, suitable for use in contact with the tissues of humans and animals without for example, undue toxicity, irritation, or allergic response, and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspending or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

Disclosed herein is the development of specific and broad-spectrum inhibitory peptides to CRISPR Cas9 variants is disclosed herein. A $1 \times 10^8$ phage displayed peptide library was synthesized and screened for phage that bind Cas9 protein complexed with gRNA (Cas9 RNP). This was done to identify peptides with affinity for Cas9. After three rounds of biopanning against Cas9 RNP using the 22-mer random peptide library, target-specific peptide pools were analyzed for enrichment, high stability, and potential for protein-protein interaction. The top 200 peptides identified from this analysis were synthesized and used to screen for inhibition of Cas9 cleavage activity using the recently described high-throughput (HT) fluorescence resonance energy transfer (FRET)-based activity assay and denaturing polyacrylamide gel electrophoresis (PAGE). See Seamon K J, Light Y K, Saada E A, Schoeniger J S, Harmon B. 2018. Versatile High-Throughput Fluorescence Assay for Monitoring Cas9 Activity. Analytical Chemistry 90:6913-6921.

Eleven peptides were confirmed as inhibitors of *S. pyogenes* (Spy) Cas9 in the direct PAGE secondary assay. Of the inhibitors that reduced Spy Cas9 mediated cleavage, one also blocked the activity of *C. jejuni* (Cje) Cas9, three inhibited *S. aureus* (Sau) Cas9 activity, and one blocked all three Cas9 variants.

Error prone PCR was used to generate a mutant library based on the eleven SpyCas9 peptide inhibitors and subsequent screening generated an additional 17 mutant peptide (MP) inhibitors with reduced $IC_{50}$ in comparison to the original peptide, four MPs were specific for SpyCas9 and five MPs had significantly reduced $IC_{50}$ for all three Cas9 variants. It is believed that this is the first identification of broad spectrum anti-CRISPR therapeutics that block Spy, Cje and Sau Cas9.

Accordingly, specific and broad-spectrum inhibitory peptides to CRISPR Cas9 are disclosed herein. A method of making and using these peptides with therapeutic CRISPR Cas9 (to improve desired targeting) or against harmful CRISPR Cas9 components (already active in a patient) is also disclosed. The peptides combined with a delivery system is also disclosed.

As briefly mentioned above, CRISPR Cas9 is a bacterial derived gene editing system. It employs a nucleic acid sequence capable of recruiting a CRISPR-associated (Cas) protein to achieve genetic modification. An exemplary CRISPR component includes those having a trans-acting CRISPR RNA (tracrRNA) and CRISPR RNA (crRNA) fused into a single, synthetic 'guide RNA' that directs a Cas nuclease (Cas9) to virtually any desired DNA sequence (see, e.g., FIG. 1). The synthetic guide RNA (gRNA) can include at two different portions: a first portion including the tracrRNA, the biding scaffold for the Cas protein, and a second portion, crRNA which includes a 17-20 nucleotide sequence complementary to a specific genomic sequence that binds to a desired genomic target sequence. The chimeric tracrRNA-crRNA sequence facilitates binding and recruitment of the endonuclease (Cas9), and provides site-specificity to the target nucleic acid, thereby allowing Cas9 to selectively introduce site-specific breaks in the target. FIG. 1 and FIG. 2A-2C show exemplary CRISPR components. FIG. 1 shows an exemplary CRISPR component that includes a guiding component 90 to bind to the target sequence 97, as well as a nuclease 98 (e.g., a Cas nuclease or an endonuclease, such as a Cas endonuclease) that interacts with the guiding component and the target sequence. As can be seen, the guiding component 90 includes a targeting portion 94 configured to bind to the target sequence 97 of a genomic sequence 96 (e.g., a target sequence having substantially complementarity with the genomic sequence or a portion thereof). In this manner, the targeting portion confers specificity to the guiding component, thereby allowing certain target sequences to be activated, inactivated, and/or modified.

The guiding component 90 also includes an interacting portion 95, which in turn is composed of a first portion 91, a second portion 92, and a linker 93 that covalently links the first and second portions. The interacting portion 95 is configured to recruit the nuclease (e.g., a Cas nuclease) in proximity to the site of the target sequence. Thus, the interacting portion includes nucleic acid sequences that provide preferential binding (e.g., specific binding) of the nuclease. Once in proximity, the nuclease 98 can bind and/or cleave the target sequence or a sequence in proximity to the target sequence in a site-specific manner.

In one instance, the first portion can include a crRNA sequence, a consensus sequence derived from known crRNA sequences, a modified crRNA sequence, or an entirely synthetic sequence known to bind a Cas nuclease or determined to competitively bind a Cas nuclease when compared to a known crRNA sequence.

The second portion can include a tracrRNA sequence, a consensus sequence derived from known tracrRNA sequences, a modified tracrRNA sequence, or an entirely synthetic sequence known to bind a Cas nuclease or determined to competitively bind a Cas nuclease when compared to a known tracrRNA sequence.

The linker can be, for example, one or more transcribable elements, such as a nucleotide or a nucleic acid, or including one or more chemical linkers. Further, the linker can be derived from a fragment of any useful tracrRNA sequence (e.g., any described herein). The first and second portions can interact in any useful manner. For example, the first portion can have a sequence portion that is sufficiently complementary to a sequence portion of the second portion, thereby facilitating duplex formation or non-covalent bonding between the first and second portion. In another example, the second portion can include a first sequence portion that is sufficiently complementary to a second sequence portion, thereby facilitating hairpin formation within the second portion.

Figure 2A:
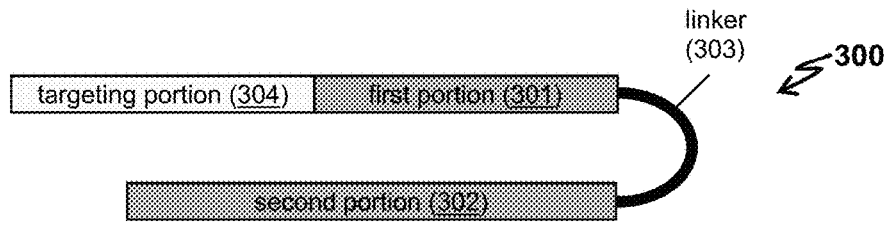
FIGS. 2A-2C are schematics showing exemplary CRISPR components.
Figure 2B:
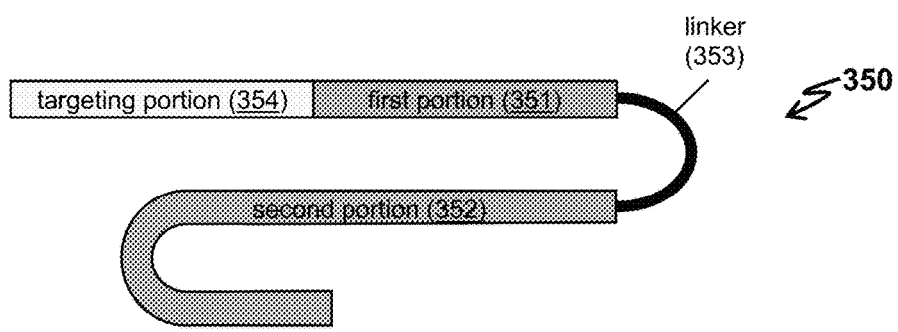
Figure 2C:
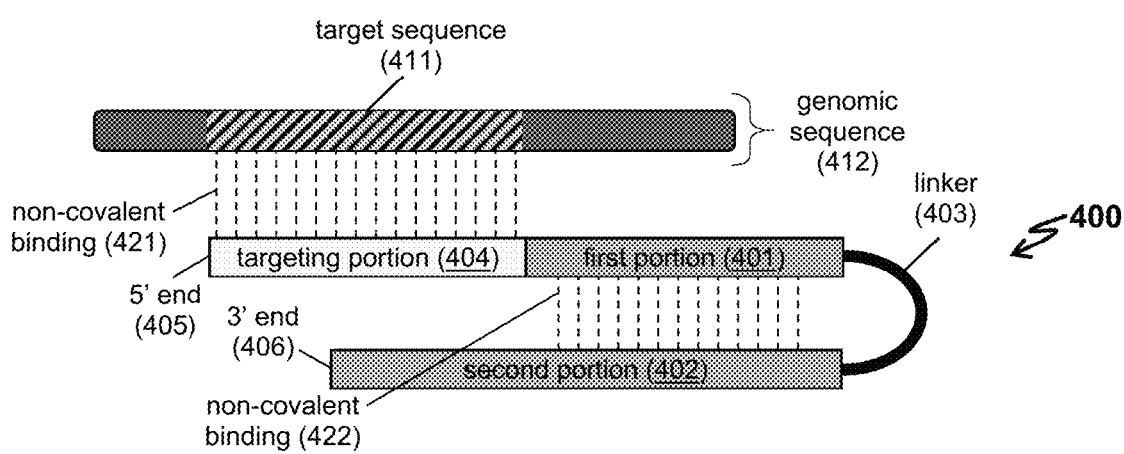

FIG. 2(A) shows a non-limiting guiding component 300 having a targeting portion 304, a first portion 301, a second portion 302, and a linker 303 disposed between the first and second portions. FIG. 2(B) shows another non-limiting guiding component 350 having a targeting portion 354, a first portion 351, a second portion 352 having a hairpin, and a linker 353 disposed between the first and second portions. FIG. 2(C) shows non-limiting interactions between the guiding component 400, the genomic sequence 412, and the first and second portion 401,402. As can be seen, the target sequence 411 of the genomic sequence 412 is targeted by way of non-covalent binding 421 to the targeting portion 404, and secondary structure can be optionally implemented by way of non-covalent binding 422 between the first portion 401 and the second portion 402. The targeting portion 404, first portion 401, linker 403, and second portion 402 can be attached in any useful manner (e.g., to provide a 5' end 405 and a 3' end 406).

This CRISPR/Cas system can be adapted to control genetic expression in targeted manner, such as, e.g., by employing synthetic, non-naturally occurring constructs that use crRNA nucleic acid sequences, tracrRNA nucleic acid sequences, and/or Cas polypeptide sequences, as well as modified forms thereof.

Additional Cas proteins and complexes are described in Makarova K S et al., "Evolution and classification of the CRISPR-Cas systems," *Nat. Rev. Microbiol.* 2011; 9:467-77, which is incorporated herein by reference in its entirety.

In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the disclosed technology, nickases may be used for genome editing via homologous recombination.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, the CRISPR component includes ds plasmid DNA, which is modified to express RNA and/or a protein. In other embodiments, the CRISPR component is supercoiled and/or packaged (e.g., within a complex, such as those containing histones, lipids (e.g., lipoplexes), proteins (e.g., cationic proteins), cationic carrier, nanoparticles (e.g., gold or metal nanoparticles), etc.), which may be optionally modified with a nuclear localization sequence (e.g., a peptide sequence incorporated or otherwise crosslinked into histone proteins, which comprise the histone-packaged supercoiled plasmid DNA). Other exemplary histone proteins include H1, H2A, H2B, H3 and H4, e.g., in a ratio of 1:2:2:2:2 with optional nuclear localization sequences.

The CRISPR component can include a promoter sequence(s), expression control sequence(s) that controls and regulates the transcription and translation of another DNA sequence, and signal sequence(s) that encodes a signal peptide. The promoter sequence can include a DNA regulatory region capable of binding RNA polymerase in a cell and initiating transcription of a downstream (3' direction) coding sequence. For purposes of the present disclosed technology, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

In addition, the CRISPR components can be formed from any useful combination of one or more nucleic acids (or a polymer of nucleic acids, such as a polynucleotide). Exemplary nucleic acids or polynucleotides of the disclosed technology include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a (β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids, chimeras, or modified forms thereof. Exemplary modifications include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present disclosure may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof).

The CRISPR component can be employed to target a nucleic acid sequence (e.g., present in the host's genomic sequence and/or the pathogen's genomic sequence). In one instance, the target sequence can include a sequence present in the host's genomic sequence in order, e.g., activate, inactive, or modify expression of factor or proteins within the host's cellular machinery. For instance, the target sequence can bind to one or more genomic sequences for an immunostimulatory protein that, upon expression, would enhance the immune response by the host to an infection. Pathogens are known to down-regulate proteins that would otherwise assist in recognizing non-self protein motifs. Thus, in another instance, the target sequence can bind to one or more regulator proteins and enhance their transcription and expression. In yet another instance, one or more polypeptides may be up-regulated, as compared to the normal basal rate, and such up-regulation may be modified by the presence of the pathogen. Accordingly, the target sequence can be employed to bind to one or more up-regulated polypeptides in order to inactivate or repress transcription/expression of those polypeptides.

In yet another instance, the target sequence can be employed to activate, inhibit, and/or modify a target sequence (e.g., associated with the presence of a pathogen, a tumor, etc.). For instance, the target sequence can be configured to activate one or more target sequences encoding proteins that promote programmed cell death or apoptosis (e.g., of the pathogen or of particular tissue types, such as metastatic growths, tumors, lesions, etc.). For instance, the target sequence can be configured to inactivate or modify one or more target sequences encoding proteins that are suppressed by the pathogen. Exemplary target sequence (e.g., in a pathogen) includes, without limitation, a nucleic acid sequence encoding a virulence factor (e.g., a lipase, a protease, a nuclease (e.g., a DNAse or an RNase), a hemolysin, a hyaluronidase, an immunoglobulin protease, an endotoxin, or an exotoxin), a cell surface protein (e.g., an adhesion), an envelope protein (e.g., a phospholipid, a lipopolysaccharide, a lipoprotein, or a polysaccharide), a glycoprotein, a polysaccharide protein, a transmembrane protein (e.g., an invasin), or a regulatory protein.

The CRISPR component can be employed to activate the target sequence (e.g., the Cas polypeptide can include one or more transcriptional activation domains, which upon binding of the Cas polypeptide to the target sequence, results in enhanced transcription and/or expression of the target sequence), inactivate the target sequence (e.g., the Cas polypeptide can bind to the target sequence, thereby inhibiting expression of one or more proteins encoded by the target sequence; the Cas polypeptide can introduce double-stranded or single-stranded breaks in the target sequence, thereby inactivating the gene; or the Cas polypeptide can include one or more transcriptional repressor domains, which upon binding of the Cas polypeptide to the target sequence, results in reduced transcription and/or expression of the target sequence), and/or modify the target sequence (e.g., the Cas polypeptide can cleave the target sequence of the pathogen and optionally inserts a further nucleic acid sequence).

A guiding component may be selected to target any target sequence. In some embodiments, the target sequence is a sequence within a genome of a host (e.g., a host cell) or a pathogen (e.g., a pathogen cell). In some embodiments, the guiding component is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guiding component is less than about 75, 50, 45, 40, 35, 30, 25, 20, 15, 12, or fewer nucleotides in length. The ability of a guiding component to direct sequence-specific binding of a CRISPR complex to a target sequence may be assessed by any suitable assay. For example, the components of a CRISPR system sufficient to form a CRISPR complex, including the guiding component to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target sequence may be evaluated in a test tube by providing the target sequence, components of a CRISPR complex, including the guiding component to be tested and a control guiding component different from the test guiding component, and comparing binding or rate of cleavage at the target sequence between the test and control guiding component reactions.

Peptides are a medium between proteins and small molecules. In contrast, to large proteins, peptides can be engineered to penetrate the cell membrane, they are less likely to result in side effects in comparison to small molecules, and they are easy to produce and modify. Although Acr proteins are small (85-185 amino acids) they are still substantially larger, e.g., 4 to 8 times larger than peptides. In general, peptides can penetrate further into tissues, they are less immunogenic than proteins and antibodies, they have lower manufacturing costs, and have higher activity and greater stability (can be dried and stored at room temperature). In addition, chemistry advances have begun to reduce the challenges associated with peptide therapeutics, for example pharmacokinetic properties of peptides can be modulated through amino acid or backbone changes, inclusion of non-natural amino acids, and cyclization and the introduction of D-amino acids to protect peptides from peptidase attack. See AlDeghaither D, Smaglo B G, Weiner L M. 2015. Beyond peptides and mAbs—current status and future perspectives for biotherapeutics with novel constructs. J Clin Pharmacol 55 Suppl 3: S4-20; Borghouts C, Kunz C, Groner B. 2005. Current strategies for the development of peptide-based anti-cancer therapeutics. J Pept Sci 11:713-26; and Fosgerau K, Hoffmann T. 2015. Peptide therapeutics: current status and future directions. Drug Discovery Today 20:122-128.

The term peptide, as used herein, is a chain of amino acids, derived from two or more amino carboxylic acid molecules (the same or different) by formation of a covalent bond from the carbonyl carbon of one to the nitrogen atom of another with formal loss of water. Peptides have shorter chain lengths than proteins, and are larger than species commonly designated as small molecules. A peptide has 50 or fewer amino acid residues in the chain, such as 3 to 48, 6 to 32, or 17 to 22. In an embodiment, only peptides that are artificially synthesized and do not occur in nature are covered by the peptides and their analogs disclosed herein.

The term "analog" as used herein referring to a peptide means a modified peptide wherein one or more amino acid residues of the peptide have been substituted by other amino acid residues, and/or wherein one or more amino add residues have been deleted from the peptide, and/or wherein one or more amino acid residues have been added to the peptide. Such addition or deletion of amino acid residues can take place at the N-terminal of the peptide and/or at the C-terminal of the peptide.

In an embodiment, the peptides with anti-CRISPR activity disclosed herein may have a number average molecular weight of about 2000 g/mol to about 3000 g/mol, such as about 2100 to about 2800 g/mol, or about 2200 to about 2700 g/mol. In another embodiment, the peptide sequences disclosed herein may be part of a larger peptide, having 50 or fewer amino acid residues, and having a number average molecular weight of about 9000 g/mol to about 2200 g/mol, such as about 2500 to about 7500 g/mol, or about 3000 to about 6000 g/mol Screening phage display libraries was used to identify peptides that selectively bind with high affinity to individual targets. To discover peptides with high affinity for Cas9, a random peptide library on T7 was generated and screened against immobilized Cas9 protein complexed with gRNA (Cas9 RNP). Cas9 from *S. pyogenes* (Spy) was used for phage panning and initial experiments. SpyCas9 is the most widely used Cas9 for genome editing. The phage library constructed had approximately $1 \times 10^8$ distinct 22 amino acid peptides that were incubated with immobilized SpyCas9 RNP followed by extensive washes to remove weak binders and stringent elution conditions to isolate strong binders. Deep sequencing of the unselected and selected phage libraries using the ILLUMINA sequencing platform allowed for an in-depth evaluation of the enrichment landscapes in peptide sequences and amino acid substitutions. The length of 22 mer units was selected to optimize between the secondary structure diversity and size of peptides. Some shorter chains were found to be useful in this process though.

After three rounds of biopanning against SpyCas9 RNP, potent candidates were identified according to their high frequencies after each panning outcome using NGS analysis. The top peptides were synthesized for further screening of Cas9-mediated cleavage activity using the recently developed high-throughput (HT) fluorescence resonance energy transfer (FRET)-based activity assay.

Then the top eleven peptide inhibitors that demonstrated activity against SpyCas9 in the HT FRET-based assay and secondary gel-based analysis were mutated to create a subsequent phage library of evolutionary peptide variants. This mutant library was screened by phage panning against SpyCas9.

The top peptides identified in the second phage display screen were synthesized and screened against SpyCas9, SauCas9 and CjeCas9 in the HT FRET assay to obtain broad spectrum inhibitors. This resulted in identification of several peptides that are inhibitory across the Cas9 variants with $IC_{50S}$ in the range of 20-75 µM and are effective in both cell free and cell-based assays. These peptides are identified in Table 1. The originally identified peptides are designated by "Peptide" before the number, the mutant peptides that were identified by screening the randomly mutated peptide phage library are identified with just a number underneath the peptide from which they are a mutant analog.

TABLE 1

| Peptide name | Sequence | SEQ ID NO: |
|---|---|---|
| Peptide 50 | LYYRIMLSCPKYYPCELVGHTS | 1 |
| 50-2-13 | LNHRIMLSCPKYYLYELVGHTS | 2 |
| 50-20-14 | LYLRIMLSCPKNNPCGLVGHTS | 3 |
| 50-2-16 | LNHRIMLSCPKYYLYELVGHTS | 4 |
| Peptide 60 | VCAFSADESLLIRRRHQRRRAG | 5 |
| 60-1-10 | VRVFSAYERLLIRRRRRRRRAG | 6 |
| 60-1-56 | VSAYSADESLLIRRRRRRRRAG | 7 |
| Peptide 63 | LNVKIGNAHLTTIMSTMPLVLC | 8 |
| 63-2-27 | PNVKIGKAHLTTIMSTMPLIIC | 9 |
| 63-2-87 | LNVKIENAHLTTNLSTMPLVLC | 10 |
| Peptide 82 | KERRRSLMQLSVKSNSLFLGGT | 11 |
| 82-2-12 | KERHRSLMRTTVKYYSLCLGGT | 12 |
| 82-2-21 | KERRRSMMQLSVKSYTLFLGGT | 13 |
| 82-2-28 | RERRRSLIQISVKSYPLFLGGT | 14 |
| Peptide 90 | DRSHKILLRYNGCHYRLLQRSL | 15 |
| 90-1-18 | DRSQKIFLRYNRCRYRLLQRGL | 16 |
| 90-1-27 | NRSHKILLHYNGCHYRLFLRSL | 17 |
| 90-1-50 | DGSLKILLRYNGCHYRLLQRSL | 18 |
| 90-2-5 | DRSHKILLRHSGCLYRFLQRYL | 19 |
| 90-2-18 | DRSHKILLCYNGRNKRLLLRRL | 20 |
| Peptide 99 | -----RRSHIAWLLAMSLTWYS | 21 |
| 99-1-1 | GDPNSRRSHIARLLAMSLTWYS | 22 |
| 99-2-2 | RDPNSRRSHIARLLAMSLTWYS | 23 |
| Peptide 15 | IAGFRREWFNQNTYFENWHADR | 24 |
| Peptide 73 | RLYHQCFLACLIDRQSPRNV-- | 25 |
| Peptide 61 | LRQISNTSIVMGTTPSSVAVCG | 26 |
| Peptide 80 | TESIRSYFAMTIRRNH------ | 27 |
| Peptide 91 | VYDFYRMLSHFFLKGPSR---- | 28 |

*Underlined letters indicate substitutions from the original peptide.

A cell-based assay was conducted on these peptides to measure the peptide inhibition of Cas9 editing. The originally identified peptides were shown to inhibit SpyCas9 activity by 20-35% in a cellular context (A549 reporter cells), without cell toxicity. This indicated their potential utility as off switches for SpyCas9.

Through additional experimentation, mutant peptides were identified that had higher maximal inhibition percentages, e.g., greater than about 50%, such as about 70% to about 35%, or about 60% to about 40%, or 55% to about 45%, and lower $IC_{50}$ s, e.g., 50 μM or less, such as about 5 to 50 μM, about 20 to 40 μM, or about 25 to 351 μM. $IC_{50}$ is the half maximal inhibitory concentration.

In addition, several of these peptides were shown to have inhibitory activity (e.g., $IC_{50}$ s, of 50 μM or less against two or three of SpyCas9, CjeCas9, and SauCas9.

A binding assay was also performed, as disclosed below, to identify the mechanism of action of the peptide inhibitors. This revealed that some of the peptides disclosed herein, Peptide 60 and 99, blocked Cas9 activity by reducing binding of the Cas9 RNP to the DNA substrate. However, Peptides 15, 90, 91, and 73 did not reduce substrate binding, suggesting that they block cleavage through another mechanism.

In certain embodiments, the anti-CRISPR peptides were shown to inhibit cleavage of Cas9 agents. A 15% Urea PAGE assay was performed to directly measure the inhibition of both the RuvC and HNH nuclease domains individually. The majority of the peptides did not demonstrate significant inhibition in this direct secondary assay, but there were 11 hit peptides that reduced the signal relative to the controls for either RuvC or HNH cleavage (see FIG. 4B).

Accordingly, two subsets of these anti-CRISPR peptides were determined: peptides that block Cas9 RNP binding to the target DNA (Peptide 15, 50, 60, 73, 90, 80, 91 and 99 and their analogs) and peptides that inhibit CACs9 RNP cleavage by another mechanism (Peptides 61, 63, and 82 and their analogs).

The peptides disclosed herein with anti-CRISPR activity can be made using established techniques, such as those used by Integrated DNA Technologies. The methods used in the Examples below can be used with equipment from, for example, Thermo Fisher Scientific.

The present constructs can be formulated, for example, for subcutaneous (SC), intranasal (IN), aerosol, intravenous (IV), intramuscular (IM), intraperitoneal (IP), oral, topical, transdermal, or retro-orbital delivery. Exemplary dosages include, e.g., about 0.001 g (peptide)/kg (body wt.) to about 0.2 g/kg, such as, 0.005 g/kg to about 0.15 g/kf, or about 0.01 to 0.1 g/kg. Daily doses can be given from 2 to 10 days, such as 2 to 8, or 3 to 5 days. Certain peptides may vary the dosage.

The anti-CRISPR peptide can be provided to a patient along with (e.g. at the same time or within 2 hours, such as within 30 minutes, or within 10 minutes before or after) a therapeutic CRISPR-Cas9 agent. In this case, an effective amount of anti-CRISPR peptides would be used to inhibit cleavage or block binding of unwanted interactions (e.g. off-target editing) of the CRISPR-Cas9 agent, thereby improving the targeting of the CRISPR agent. In another embodiment, the anti-CRISPR peptides are provided along with or after the CRISPR-Cas9 agent to inactivate further activity after a certain period of time, such as when a treatment is deemed complete or medically sufficient.

In another embodiment, the anti-CRISPR peptide can be provided to a patient that has been adversely affected by a harmful CRISPR-Cas9 agent. In this case, it would be used in effective amounts to halt the activity of the harmful CRISPR-Cas9 agent. In another embodiment, a combination of different anti-CRISPR peptides can be used together in a single dosage or combined in a treatment regimen of separate doses, or combined in a single pharmaceutically acceptable carrier. In an embodiment, one anti-CRISPR peptide or group of anti-CRISPR peptides have activity to block binding activity of Cas9 and another anti-CRISPR peptide or group of peptides are active to block cleavage activity.

To some extent all the peptides shown in Table 1 had activity against each of SpyCas9, SauCas9, and CjeCas9. However, certain peptides displayed stronger activities as shown in the examples below.

In an embodiment, a peptide that has strong activity against CRISPR SauCas9 are provided to a patient along with a CRISPR SpyCas9 agent, or to counteract a dose of harmful CRISPR SpyCas9 agent that was already in the patient's system. For example, one or more peptides with strong activity against CRISPR SpyCas9 are selected from the group consisting of: 60-1-10, 80-2-21, 90-1-27, 50-2-16, Peptide 60, 60-1-56, 82-2-12, 90-1-18, Peptide 99, 90-2-18, 90-1-1, 90-2-2, 91-1-50, and combinations thereof, as defined by their associated sequence in Table 1. In another embodiment, one or more peptides are selected from the group consisting of: 60-1-10, 82-2-21, and 90-1-27 and combinations thereof are provided to a patient in association with a CRISPR SpyCas9 agent.

In an embodiment, a peptide that has strong activity against CRISPR SauCas9 are provided to a patient along with a CRISPR SauCas9 agent, or to counteract a dose of harmful CRISPR SauCas9 agent that was already in the patient's system. For example, one or more peptides with strong activity against CRISPR SauCas9 are selected from the group consisting of: 60-1-10, 82-2-21, 90-1-27, 50-2-16, 60-1-56, 82-2-12, 90-1-18, 90-2-18, 99-1-1, and combinations thereof, as defined by their associated sequence in Table 1. In another embodiment, one or more peptides are selected from the group consisting of: 60-1-10, 82-2-21, and 90-1-27 and combinations thereof are provided to a patient in association with a CRISPR SauCas9 agent.

In an embodiment, a peptide that has strong activity against CRISPR CjeCas9 are provided to a patient along with a CRISPR CjeCas9 agent, or to counteract a dose of harmful CRISPR CjeCas9 agent that was already in the patient's system. For example, one or more peptides with strong activity against CRISPR CjeCas9 are selected from the group consisting of: 60-1-10, 82-2-21, 90-1-27, 50-2-16, 60-1-56, Peptide 50, 63-2-87, 82-2-12, 90-1-18, 90-2-18, 99-1-1, and combinations thereof, as defined by their associated sequence in Table 1. In another embodiment, one or more peptides are selected from the group consisting of: 60-1-10 and 82-2-21 and combinations thereof are provided to a patient in association with a CRISPR CjeCas9 agent.

Of the original 11 identified peptides, six were identified with micromolar efficacy against Cas9 from *S. pyogenes* (Spy), *S. aureus* (Sau) and *C. jejuni* (Cje). Peptide 15 significantly reduced activity of CjeCas9 and SpyCas9 at 100 µM (P<0.01) and 200 µM (P<0.005), Peptide 60, 90, and 91 significantly reduced activity of SauCas9 and SpyCas9 at 100 µM (P<0.005) Peptide 99 significantly reduced activity of all three Cas9 variants at 100 and 200 µM (P<0.005). Six of the mutant peptides had a significant $IC_{50}$ reduction for all Cas9 variants: peptides 60-1-10, 60-1-56, 90-1-27, 90-2-18, 82-2-12 and peptide 82-2-21.

In an embodiment where a broad-spectrum anti-CRIPSR peptide is desirable, one or more anti-CRISPR peptides may be selected from the group consisting of: 60-1-10, 82-2-21, and 90-1-27. These peptides showed particularly strong activity against all of SpyCas9, SauCas9, and CjeCas9. A broad-spectrum anti-CRISPR may be desirable in a case where an unknown harmful CRISPR component is active in a patient's system. In an embodiment, the broad spectrum anti-CRISPR peptide is a bioactive agent having an $IC_{50}$ of 200 µM or less against SpyCas9, SauCas9, and CjeCas9.

In an embodiment, the anti-CRISPR peptide is included in a formulation or composition pharmaceutically acceptable excipient (e.g., any described herein). In an embodiment, the composition including the anti-CRISPR peptide can be formulated with a plurality of particles. Such formulations can be included with a medium, excipient (e.g., lactose, saccharide, carbohydrate, mannitol, leucine, PEG, or trehalose), additive, propellant, solution (e.g., aqueous solution, such as a buffer), preservative, carrier (e.g., aqueous saline, aqueous dextrose, glycerol, or ethanol), binder (e.g., saccharide, cellulose preparation, starch paste, or methyl cellulose), filler, or disintegrator.

Pharmaceutical compositions according to the present disclosure include an effective population of peptides herein formulated to effect an intended result (e.g., immunogenic result, therapeutic result and/or diagnostic analysis, including the monitoring of therapy) formulated in combination with a pharmaceutically acceptable carrier, additive, or excipient. Pharmaceutical compositions according to the present disclosure may also comprise an additional bioactive agent or drug, such as an antibiotic or antiviral agent.

Formulations and compositions containing the particles according to the present disclosure may take the form of liquid, solid, semi-solid or lyophilized powder forms, such as, for example, solutions, suspensions, emulsions, sustained-release formulations, tablets, capsules, powders, suppositories, creams, ointments, lotions, aerosols, or patches, in unit dosage forms suitable for simple administration of precise dosages.

Methods for preparing such dosage forms are known or apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the disclosed technology.

In an embodiment, the anti-CRISPR agent can be delivered as a cargo on a nanoparticle, such as a mesonanoporous nanoparticle, or a lipid-coated nanoparticle, such as those described in commonly owned application Ser. No. 16/141,725, filed Sep. 25, 2018, incorporated herein by reference for all purposes. The nanoparticle construct can also be included in a pharmaceutically acceptable carrier or excipient. In an embodiment, more than one peptide can be loaded on the nanoparticle substrate. In an embodiment, one anti-CRISPR has activity to block binding activity of Cas9 and the other is active to block cleavage activity.

EXAMPLES

Figure 3:
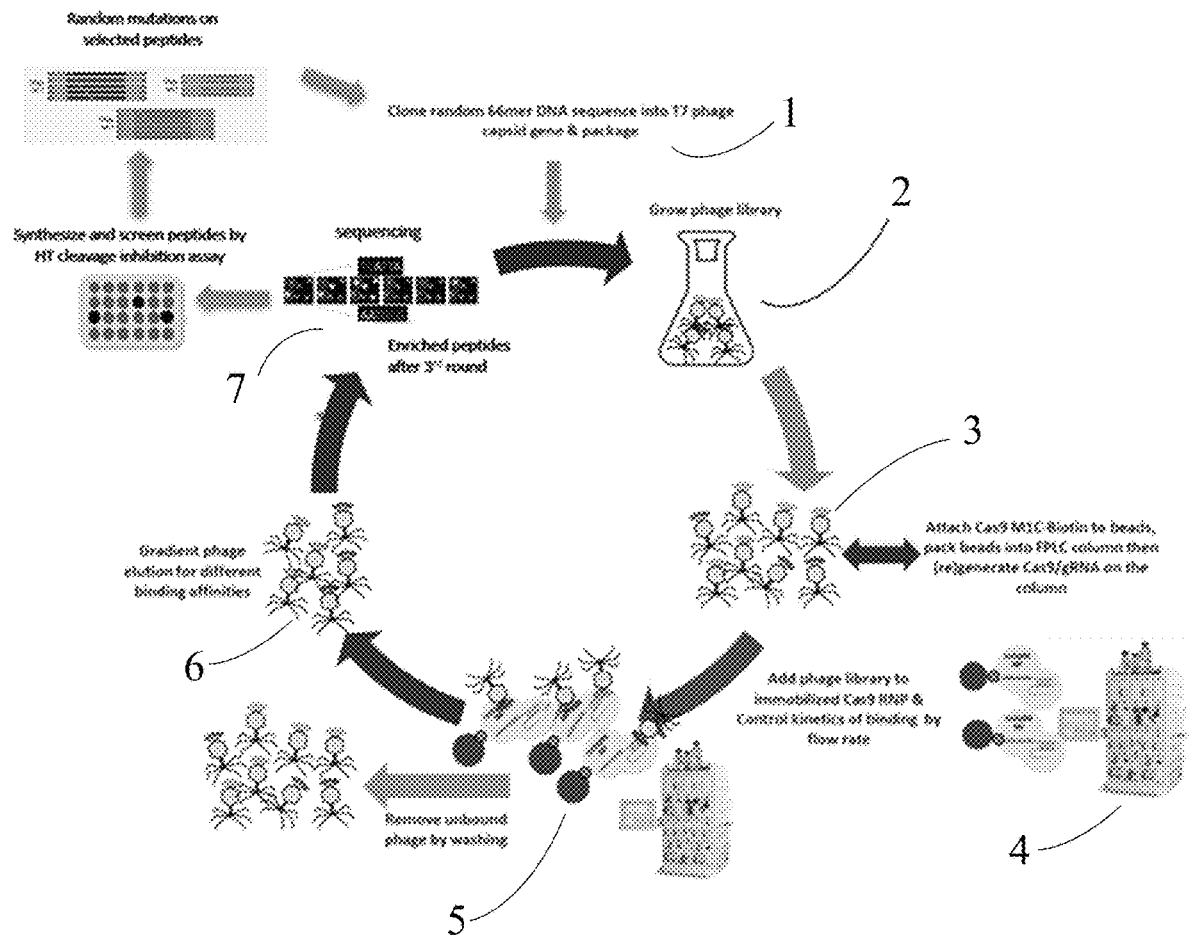
FIG. 3 is a schematic providing an overview of the synthesis process of Examples 1-4.

FIG. 3 is a schematic providing an overview of several of the examples below (Examples 1-4) screening peptide inhibitors of Cas9 using T7 phage display and FPLC system. The features of this figure are discussed more in depth below, but, briefly, a phage library was generated to display ~1×10^8 possible peptides on phage surface by cloning random oligo nucleotides fused into phage capsid genes. Biotinylated Cas9 was prepared by conjugation via single cysteine on Cas9 and immobilized as Cas9/sgRNA complex on Neutravidin or Monomeric Avidin resin columns. Phage peptides binding to RNP immobilized on Neutravidin were eluted by salt gradient, and for RNP immobilized on monomeric avidin column, biotin was used as the final eluent. The eluted phages were amplified and subjected to additional rounds of enrichment. See Wu C-H, Liu I J, Lu R-M, Wu H-C. 2016. Advancement and applications of peptide phage display technology in biomedical science. Journal of biomedical science 23:8-8, incorporated herein by reference. A total of three rounds of phage amplification, panning, and DNA sequencing was performed to identify enriched peptides with high affinity for Cas9 RNP. Additional experiments were performed with mutated versions of the most promising peptides.

Example 1: Cloning T7 Phage Library

The random 66-mer DNA oligonucleotides with EcorI/HindIII restriction enzyme sites (CCGGGATCCG|AAT-TCCNNNNNNNNNNNNNNNNNNNNNNNNNNNNNNNN-NNNNNNNNNNNNNNNNNNNNNNNNNNNNN-NNNNNTGAAAGCT|TGCGGCCGC)(SEQ ID NO: 29) was synthesized from IDT (Integrated DNA Technologies). For cloning 66-mer random DNA fragments into the phage vector, T7SELECT 10-3b (EMD MILLIPORE) was used. The vector plasmid was prepared with EcoR I/Hind III digestion and dephosphorylation of the ends with alkaline phosphatase using standard protocols. (FIG. 3, step 1)

To confirm restriction digestion, 100 ng of the digest were run on a 0.4-0.6% agarose gel at low voltage for several hours alongside uncut vector. The synthesized DNA fragments were also treated with EcoR I/Hind III restriction enzymes and ligated into the linearized vector using DNA ligation kit (NEB) incubating 16 hours at 16° C.

Example 2: In Vitro Packaging and Plaque Assay

To package the ligated DNA of Example 1 into phage particles, the T7SELECT Packaging Extract (EMD MILLIPORE) was used. Ten reactions of 5 µl of ligation reaction per 25 µl extract were gently mixed and incubated at room temperature (22° C.) for 2 hrs. Each reaction was stopped by adding 270 µl sterile LB (lysogeny broth) medium. A plaque assay described below was performed to determine the number of recombinants generated. For the plaque assay, host strain, E. coli BLT 5615 (EMD MILLIPORE), was inoculated in M9 TB and incubated with shaking at 37° C. to an OD600=1.0. A series of dilutions of the sample were prepared using LB medium as the diluent. 250 µl of host cells and 100 µl of the phage dilution was mixed into each tube and 3 ml molten top agarose was added to the tube. The contents were poured onto a prewarmed (37° C.) LB/carbenicillin agar plate and incubated for overnight at room temperature. The plaques were counted to calculate the phage titer. (FIG. 3, step 1)

Example 3: Growth of T7 Lysates

A ratio of $10^6$ phage particles (packaging reaction) per 10 ml of E. coli BLT 5615 from Example 2 were mixed in a sterile 50 ml tube. 1 ml aliquots of the phage/host mixture were transferred into sterile 15 ml tubes. 10 ml molten top agarose at 45-50° C. were added to each tube. The contents of the tube were immediately poured onto an LB/carbenicillin plate. Top agarose was evenly spread by gently swirling the plate and incubated overnight at room temperature. To elute the phage, each plate was covered with 10 ml of Phage Extraction Buffer (20 mM Tris-HCl, pH 8.0, 100 mM NaCl, 6 mM MgSO$_4$) and place on a level surface at 4° C. from 2 h to overnight and harvested. The titer of the amplified library was determined by plaque assay. T7 phages were further propagated on logarithmically growing E. coli BLT 5615 by diluting a fresh overnight culture in 500 volumes of M9 TB, incubating with shaking for 3.5-4 h at 37° C. to OD600 of 0.6-0.8 and then infecting with a phage stock. A plating assay was used to determine the number of phage present in samples. (FIG. 3, step 2.)

Example 4: SpyCas9 Column Preparation and Panning

SpyCas9M1C/noCys protein and Cas9 variants were expressed and purified as following. The Cas9 plasmid was transformed into E. coli BL21(star)DE3, grown to an OD600 of ~0.5, induced with 0.25 mM IPTG, and grown at 20° C. for 20 h. The pellets were lysed in buffer A [50 mM Tris-HCl, pH 7.5, 0.5 mM TCEP] with 500 mM NaCl and 10% glycerol by an Avestin EmulsiFlex-C5 homogenizer. The lysate was clarified and purified by Ni-NTA chromatography with a linear gradient of 10 to 500 mM imidazole in the above buffer. The eluted protein was dialyzed overnight against 1 L of buffer B [20 mM HEPES, pH 8, 0.5 mM TCEP, 10% glycerol] with 200 mM KCl in the presence of ⅓₀th mass of TEV protease. MacroPrep High S cation exchange chromatography was performed with a linear gradient of 100 to 1000 mM KCl in buffer B. The eluted protein was passed through a 5 mL Ni-NTA column, and the flow-through was collected, concentrated, exchanged into storage buffer [20 mM HEPES, pH 8, 150 mM KCl, 1 mM TCEP, 20% glycerol], flash frozen, and stored at –80° C. A biotin group was attached to Cas9M1C by incubating with 20-fold molar excess Ez-Link Maleimide-PEG11-biotin at pH of 7.0 overnight at 16° C. Unreacted Ez-Link Maleimide-PEG11-biotin was removed by buffer exchange (200 mM KCl, 50 mM Tris-HCl (pH 7.5), 10% glycerol, 1 mM TCEP) using a Econo-Pak 10 DG desalting column (Bio-Rad, CA).

An FPLC (Fast protein liquid chromatography) system was sterilized by extensive washes with 1M NaOH followed by DI (deionized) water and 1 ml empty FPLC columns were packed with NeutrAvidin or with Monomeric Avidin resins. The column was connected to FPLC and washed and calibrated with 3 volumes of DI water followed by Cas9 buffer (50 mM Tris-HCl (pH 7.5), 200 mM KCl, 10% glycerol).

Before the attachment of Cas9M1C-biotin to the Avidin column, Cas9M1C-biotin was assembled with sgRNA (Cas9:sgRNA=1:2) in RT for 20 mins. 2 ml of the Cas9/sgRNA complex was bypassed the column to measure absorbance at A280 and calculate the initial amount of the protein. The bypassed SpyCas9/sgRNA was reapplied through the prepared column and the attached amount of Cas9/sgRNA was determined by the difference of absorbance area curves at A280 from before and after passing the column. (FIG. 3, step. 3)

After calibrating the column with phage buffer, phage library was applied to the column (0.2 ml/min) and subsequently washed with 3 volumes of phage buffer. (FIG. 3, step 5). The bound phages were eluted with salt gradient (150 mM to 1M NaCl$_2$) for NeutrAvidin column or 20 mM biotin for monomeric Avidin column after the salt gradient (FIG. 3, step 6) and inoculated into E. coli BLT5615 cells in log-phase growth for phage amplification. After bacteriolysis (FIG. 3, step 7), phages were recovered from the culture supernatant by centrifugation and PEG-precipitation, resuspended in PBS, and used for the next round of panning.

After 2 subsequent rounds of phage amplification, panning, and DNA sequencing, enriched sequences were identified by a bioinformatics pipeline.

Example 5: Sequencing and Analysis of Phage Library

DNA from phage enriched after three rounds of panning from Examples 1-4, was extracted using Viral DNA kit (ZYMO) and quantitated by Qubit (Thermo Fisher). The sequencing library preparation was carried by two rounds of PCR: (1) the inserted peptide coding sequences were amplified with region-specific primers that included random 8-mer sequence, a stager sequence, and partial ILLUMINA flowcell adapter sequences; (2) the full adaptor sequences and TrueSeq barcode (underlined) were extended from the first PCR product using the primers (5'-AATGA-TACGGCGACCACCGAGATCTACACTCTTTCCCTA-CACGACGCTCTTCCG-3' (SEQ ID. NO: 30) and 5'-CAAGCAGAAGACGGCATACGAGATAT-TGGCGTGACTGGAGTTCAGACGTGTGCT CTTCC-GATC-3' (SEQ ID NO: 31).

The PCR reactions contained 1×NEBNext High Fidelity PCR Master mix, 0.1 ng/µl of DNA template and 500 nM primers. A 5 µl reaction mix was aliquoted in 20 replicate wells for each sample and the number of each PCR cycle was limited to 10 cycles during amplification to reduce potential biases introduced during the amplification. After the reaction is completed, the PCR reactions were pooled and purified using the QIAquick PCR purification kit according to the manufacturer's directions. The purified PCR target library was run on a 2% (wt/vol) agarose gel along with a 50 bp ladder to separate the library DNA with full length ILLUMINA adaptors. The target library DNA was extracted from the gel using the QIAquick gel extraction kit according to the manufacturer's directions and quantified by Qubit and qPCR using Kapa Illumina library quantitation standard (ROCHE). The library was denatured and loaded at 1.4 µM with 10% PhiX on NextSeq (ILLUMINA) for HighOutput 150-cycle reads according to the manufacturer's directions.

Fastq files were generated and demultiplexed by converting the bcl files from the sequencing output and filtered by removing low quality reads (Q30>) and trimming adaptors using Fastp(67). The peptide coding sequences were parsed out by matching the conserved flank sequences without any mismatches allowed. The unique parsed sequences were translated to amino acid sequences and the counts of unique amino acid sequences were converted as count per million (CPM) after normalized with the total reads of each sample. The CMP values were compared to determine enriched peptide sequences. The Boman and instability indices were calculated using an R-package for Peptides from an internet source.

Example 6: Fluorescence Assays to Measure Cas9 Mediated Substrate Cleavage

To determine whether synthetic peptides would inhibit Cas9 cleavage activity, 200 peptide sequences were selected for chemical synthesis based on the following criteria: (1) peptides enriched after independent panning on RNP immobilized on both the Monomeric Avidin and NeutrAvidin columns, (2) Higher Boman index (>2.3), the computed potential protein-protein interaction for a given amino-acids sequence (3) a predicted instability index below 50. Theses peptides were screened at 200 µM for inhibition of Cas9 cleavage activity using the recently developed HT FRET-based assay using a dual-quencher substrate with low background and high sensitivity. See Seamon K J, Light Y K, Saada E A, Schoeniger J S, Harmon B. 2018. Versatile High-Throughput Fluorescence Assay for Monitoring Cas9 Activity. Analytical Chemistry 90:6913-6921. This assay specifically measures DNA substrate cleavage, and is able to differentiate between cleavage of a single strand of DNA and cleavage of both DNA strands.

Reactions (10 µL tubes) were set up in Cas9 reaction buffer (20 mM Tris-HCl, pH 7.5, 100 mM NaCl, 5 mM $MgCl_2$, 0.1 mM EDTA) containing 50 nM annealed DNA substrate, 1.5 µM sgRNA, and 500 nM Cas9 in the wells of a black low volume 384-well plate. The reactions were incubated for 1 hour at ambient temperature; then, 10 µL of 8 M Gdn-HCl was added to quench the reaction before the plates were covered with an aluminum seal and incubated at 80° C. for 10 minutes. The fluorescence was read in a Tecan Infinite M1000 or SPARK plate spectrofluorometer (Tecan).

Figure 4A:
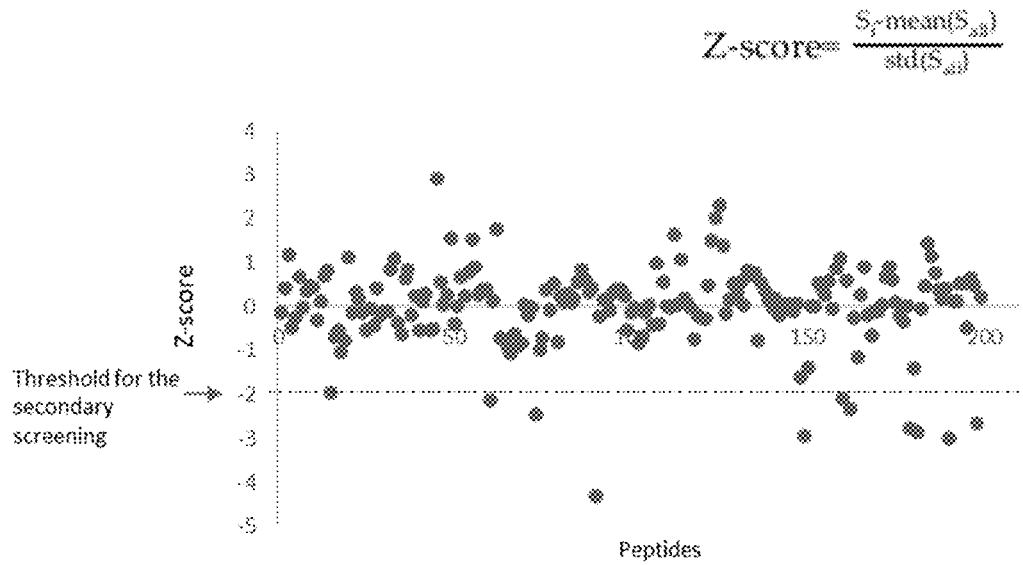
FIG. 4A is a statistical plot of Z-scores of synthesized peptides based on fluorescence representing an affinity for Cas9.

FIG. 4A shows screening of synthesized mutated peptides for Cas9 inhibition by the initial screening with FRET based high-throughput assay. The fluorescent values of 123 mutated peptides from the high throughput screening (HTS) were normalized by Cas9 and dCas9 and Z-scores were calculated by dividing the mean-subtracted fluorescent value with standard deviation of all fluorescent values. Data points are the average of three replicate wells.

Peptides with a Z-score of −2 or lower (FIG. 4A) were selected for secondary screening via a 15% Urea PAGE assay to directly measure the inhibition of both the RuvC and HNH nuclease domains individually. The majority of the peptides did not demonstrate significant inhibition in this direct secondary assay, but there were 11 hit peptides that reduced the signal relative to the controls for either RuvC or HNH cleavage (FIG. 4B).

FIG. 4A shows screening of synthesized peptides for Cas9 inhibition through the initial screening with the FRET based high-throughput assay. The fluorescent values of 200 peptides from the HTS were normalized by Cas9 and dCas9 and then Z-scores were calculated by dividing the mean-subtracted fluorescent value with standard deviation of all fluorescent values.

Figure 4B:
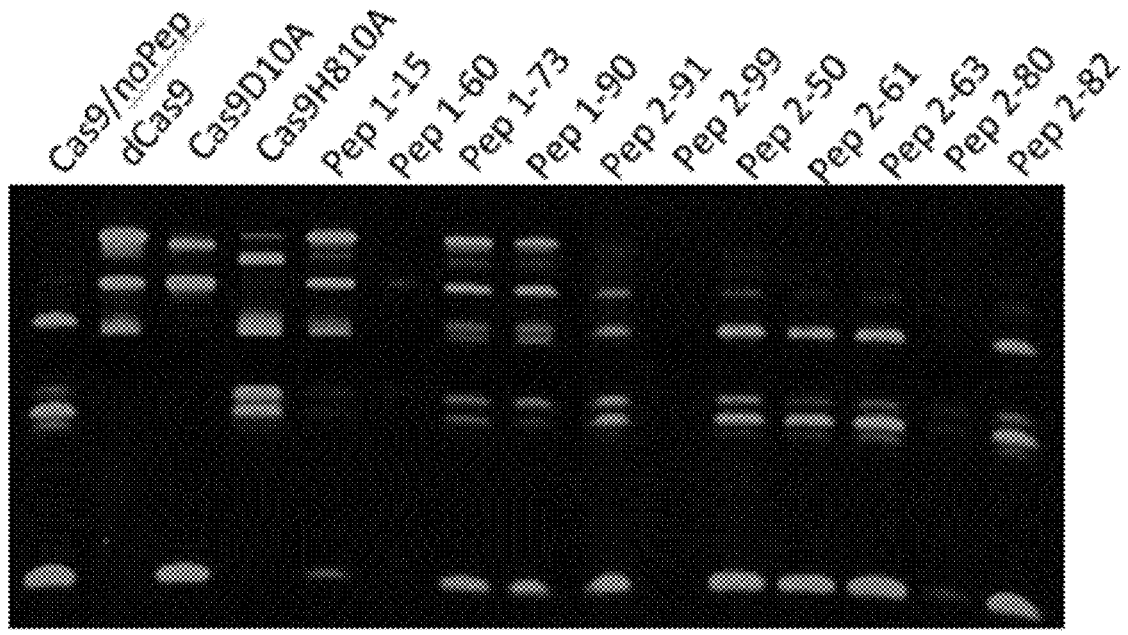
FIG. 4B is a photo showing secondary screening of peptide inhibition by cleaved dual FAM-labeled substrate on denatured gel (15% urea PAGE).

FIG. 4B shows secondary screening of peptide inhibition by cleaved dual FAM-labeled substrate on denatured gel (15% urea PAGE). The relative activity of HNH (Cas9D10A) and RuvC (Cas9H810A) domains were shown along with 11 hits identified from the primary screening. (Peptides denoted as Pep1 are from the first set of ordered peptides and peptides denoted Pep2 are from the second set. Peptides denotes as Pep are from the original phage display library.)

Figure 5:
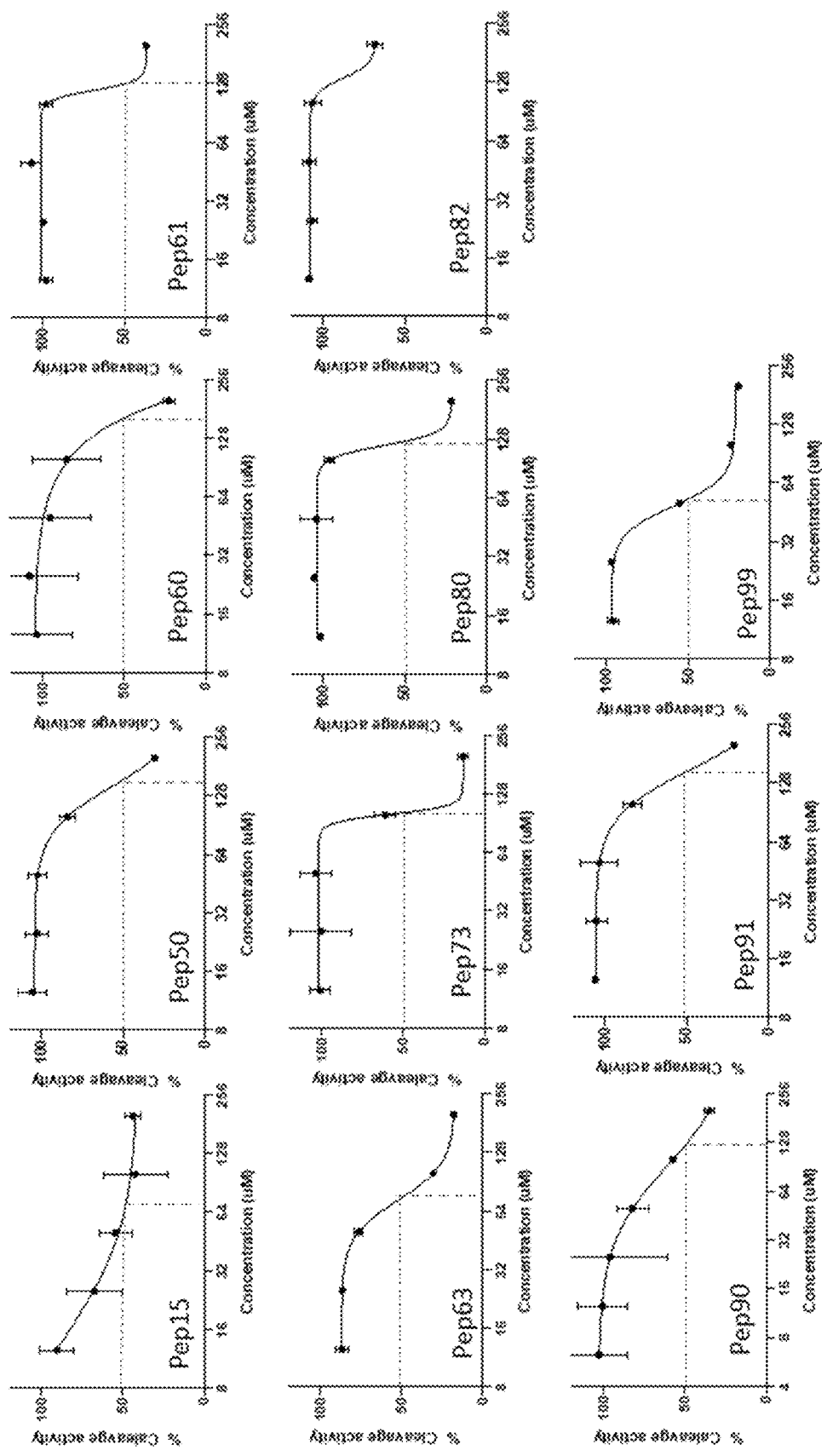
FIG. 5 are graphs showing peptides inhibiting substrate cleavage in a peptide concentration-dependent manner.

The 11 peptides that demonstrated reduced substrate cleavage in the Cas9 cleavage reaction (visualized by PAGE) at 200 µM, were further analyzed to determine the dose response. The peptides were diluted 2-fold from 200 to 12.5 µM and incubated for 1 hour with 500 nM SpyCas9, gRNA prior to addition of 50 nM FRET DNA substrate for 1 hour. As shown in FIG. 5, the peptides inhibited substrate cleavage in a peptide concentration-dependent manner. Data are the average ±SD of three replicate wells.

Example 7: Beacon DNA Binding Assay

To determine the mechanism of action of these peptide inhibitors, a binding assay was performed to determine if inhibitors are blocking Cas9 RNP binding to the DNA substrate. The beacon DNA binding assay was adapted and performed as described in Mekler V, Minakhin L, Semenova E, Kuznedelov K, Severinov K. 2016. Kinetics of the CRISPR-Cas9 effector complex assembly and the role of 3'-terminal segment of guide RNA. Nucleic Acids Res 44:2837-45. DNA probes were prepared from unmodified and chromophore-labeled DNA oligonucleotides synthesized by Integrated DNA Technologies. Equimolar amounts of synthetic complementary strands were mixed in a buffer containing 40 mM Tris, pH 7.9, 100 mM NaCl; heated for 2 min at 90° C. and slowly cooled to 20° C. The PAM-distal ends of the beacon target and non-target strands were labeled with fluorescein and Iowa Black® FQ, respectively. Both beacons mimic native target DNA and bind Cas9/sgRNA. The fluorescent signal is increased when Cas9 binds the DNA substrate and a helix forms with the target substrate strand and gRNA resulting in dissociation of oligo 3, leading to increase in fluorescent signal.

Figure 6:
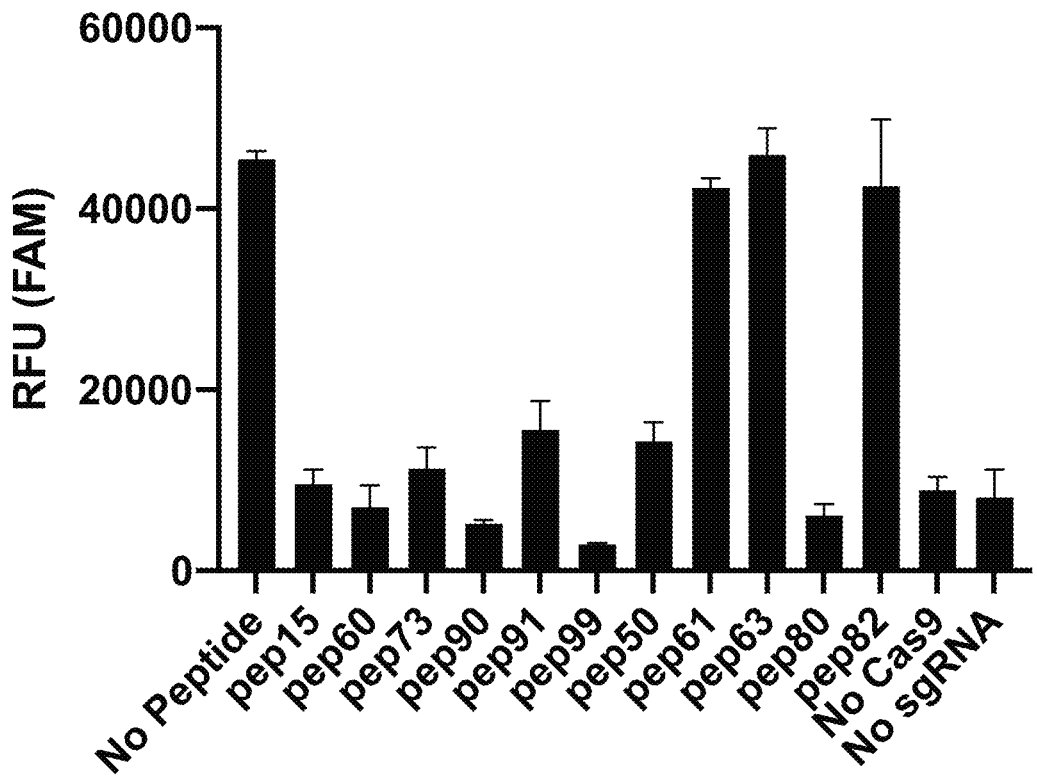
FIG. 6 is a graph showing several the synthesized peptides having binding inhibition at 200 µM against SpyCas9 (500 nM) to DNA substrate.

FIG. 6 shows several of the peptides having binding inhibition at 40 µM against SpyCas9 (500 nM) to DNA substrate (50 nM). Data are the average ±SD of three replicate wells. The fluorescence observed upon addition of Cas9 complexes was unaltered by incubation with Peptide 15, 90, 91, and 73, but is significantly reduced by Peptide 60 and Peptide 99, indicating that Peptide 60 and 99 block the interaction of SpyCas9 with the DNA substrate.

Example 8: In Vitro Cell-Based Assays

Figure 7:
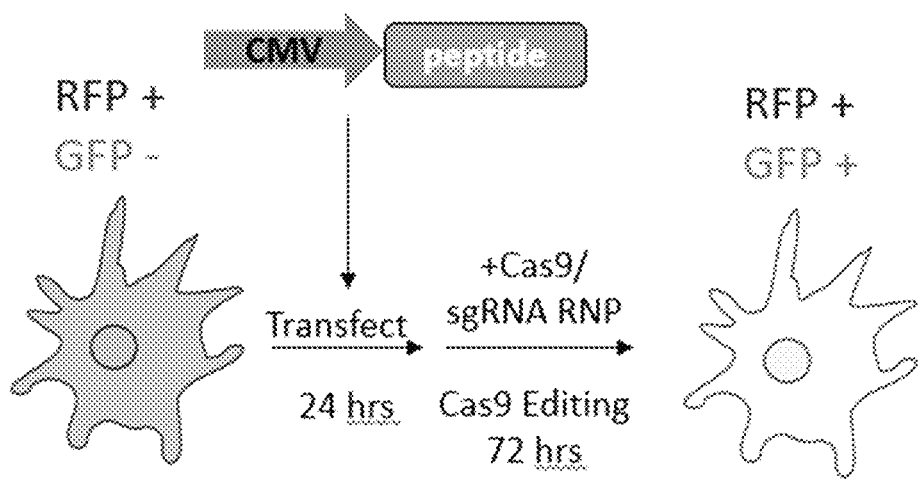
FIG. 7 is a schematic showing the cell-based reporter assay of Example 8.

The cell-based reporter assay was generated using an endonuclease surrogate reporter construct expressed in A549 cells. This construct was composed of genes encoding two fluorescent proteins (red fluorescent protein (RFP) and green fluorescent protein (GFP)) linked by the endonuclease targeting sequence. See FIG. 7. In the absence of endonuclease (e.g. Cas9) expression, the reporter was designed to express the RFP but not GFP as it is placed out of frame. Upon expression of Cas9 with a targeting gRNA, the RNP introduces a double stranded break at the target site upstream of the GFP genes leading to frameshift mutations and expression of GFP (FIG. 7). An AAVS1 protospacer and PAM sequence used for targeting by SpyCas9 RNP is in between the RFP and GFP genes. RNP targeting to the AASV1+PAM sequence in the cell's nucleus results in a DSB and error prone NHEJ will likely cause either of the GFP genes to now become in-frame and induce GFP expression. The expression of GFP is strictly dependent on the presence of nuclease activity from endonucleases that specifically recognizes the target sequence in the reporter construct. A549 reporter cells for SpyCas9 were reverse transfected with 100-500 ng of indicated plasmids using Lipofectamine, the plasmids were at a 1:1 ratio with SpyCas9 RNP. AcrIIA4 (positive control for inhibition) and a negative plasmid control (peptide sequence with similar pI that does not block cleavage) were included as controls. After 24 hours the media was changed, and 100-500 ng of SpyCas9 RNP was forward transfected using CRISPRMax (Thermo Fisher).

Figure 8:
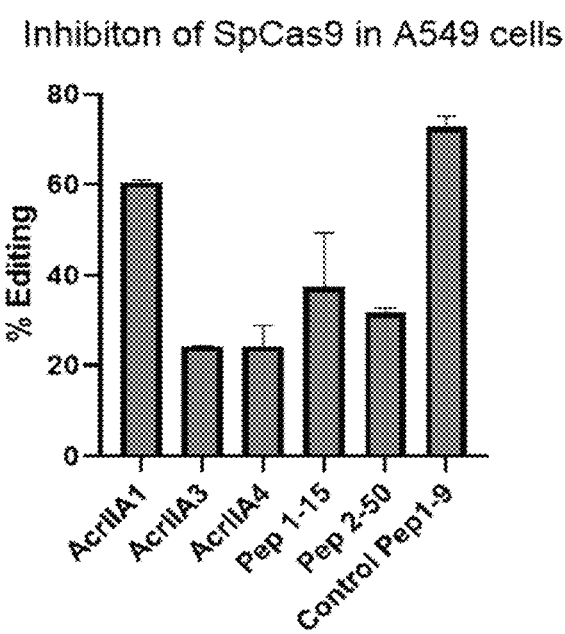
FIG. 8 is a graph showing gene editing results of the cell-based reporter assay of Example 8.

Editing was assessed at 48 hours and 72 hours post transfection using the CX7 plate imager and/or flow cytometry using an ACCURI C6 flow cytometer (BD BIOSCIENCES) with FCS EXPRESS SOFTWARE (DE NOVO SOFTWARE). Cells were counted as edited if their FL-1 fluorescence was greater than that of the no RNP control. FIG. 8 shows the relative % CRISPR editing of A549 GFP reporter cells that were reverse transfected with 500 ng of indicated plasmids 24 hours prior to forward transfection with SpyCas9 RNP. Error bars represent ±SD across technical replicates (n=2).

In these cells shown in FIG. 8, AcrIIA4 reduced editing (compared to plasmid control) by 74±2.3%, Peptide 15 reduced editing by 21±4.2%, Peptide 50 by 30±1.4%, Peptide 60 by 30±2.3%, and Peptide 90 by 35±2.1%. These results demonstrated that these peptides inhibit SpyCas9 activity by 20-35% in a cellular context, without cell toxicity, indicating their potential utility as off-switches for SpyCas9.

Example 9: Cleavage Assays with SpyCas9, SauCas9, and CjeCas9

Figure 9:
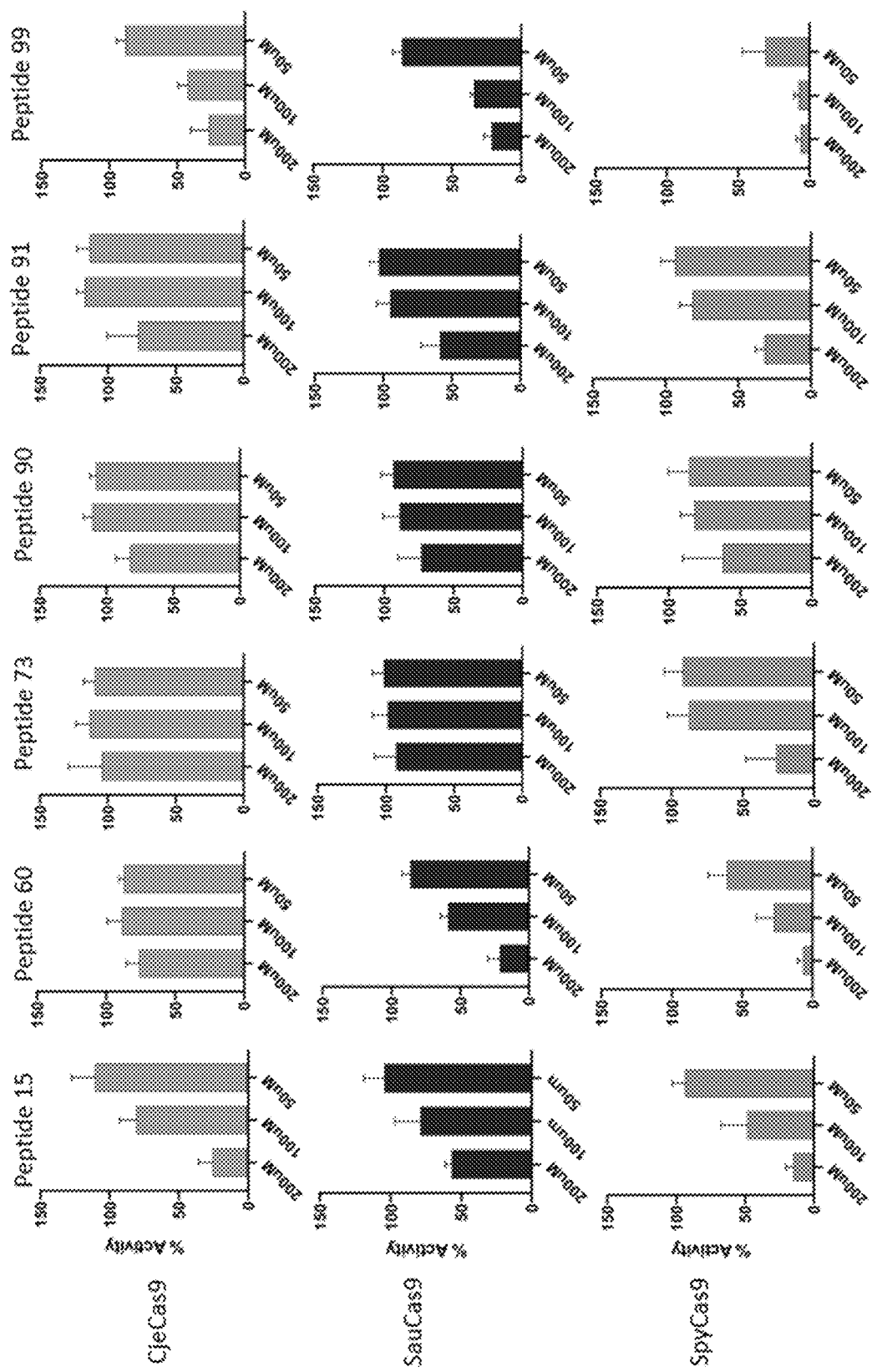
FIG. 9 is a series of graphs showing six peptides inhibition against Cas9 variants.

To evaluate the ability of identified peptides to inhibit other Cas9 variants, SauCas9 and CjeCas9 cleavage assays were used to quantitatively measure changes in activity. FIG. 9 shows six peptides inhibition against Cas9 variants. The inhibition was measured as relative fluorescent value to Cas9 without peptides (% activity) of CjeCas9 (Top), SauCas9 (middle), SpyCas9 (bottom) by FRET assay with the indicated concentration of peptides. Data are the average ±SD of eleven replicate wells from three technical replicates.

The six peptides shown in FIG. 9 demonstrated micromolar efficacy against Cas9 from S. pyogenes (Spy), S. aureus (Sau) and C. jejuni (Cje). Peptide15 significantly reduced activity of CjeCas9 and SpyCas9 and SauCas9 at 200 µM (P<0.01), Peptide 60, 90, and 91 significantly reduced activity of SauCas9 and SpyCas9 at 200 µM (P<0.005) Peptide 99 significantly reduced activity of all three Cas9 variants at 100 and 200 µM (P<0.005). However, the high IC50s of these inhibitors in vitro (50-100 uM) and the limited efficacy in cell-based assays (20-35%), suggested the need for affinity enhancement. (The leading number for each original peptide is dropped in other references in the text and Figures, e.g. 90-1-27 is the same as Peptide90-1-27.)

Example 10: Peptide Sequence Optimization by Mutant-Derived Phage Library

For affinity enhancement, the coding DNA fragments of the 11 selected peptides (see Table 1, original peptides identified by peptide preceding the numeric identified) were synthesized and random mutations were generated using an error-prone PCR protocol described below. The top 11 peptides were those that showed moderate affinity for SpyCas9. Briefly, a series of dilution and amplification steps to generate a mutagenic library that contains a range of single-nucleotide point mutations. After every four cycles of PCR amplification, a small portion of the PCR reaction mixture was transferred to a fresh tube and the process was continued for a total of 64 cycles of PCR with 16 serial transfer steps. The reaction mix contains 1 µM forward primer, 1 µM reverse primer, 1 mM each of dCTP&dTTP and 0.2 mM each of dATP&dGTP, 1× PCR buffer (10 mM Tris-HCl, pH 8.3, 1.5 mM MgCl2, and 50 mM KCl), 5.5 mM MgCl2. The PCR reaction mixture was dispensed into tubes 1 through 16 by adding 96 µL to tube 1 and add 88 µL to tubes 2-16. 2 µL of the DNA template was added to tube 1 and 1 µL of freshly prepared MnCl2 solution and 1 µL of Taq DNA polymerase were added to the PCR reaction tube at annealing temperature (55° C.). After 4 cycles of PCR amplification were performed, 10 µL of the PCR reaction was transferred from tube 1 to tube 2 and 1 µL of freshly prepared MnCl2 solution and 1 µL, of Taq DNA polymerase to the PCR reaction tube and 4 cycles of PCR amplification was performed. The PCR steps were repeated from tubes 3 through 16 to create a mutagenic library by serial dilution amplification. The reaction products were then analyzed and pooled to create a random library for directed evolution on a phage peptide library. The cloning and phage panning procedures were same as described previously, except only Monomeric Avidin column was used with 20 mM biotin as eluent after extensive washes with 200 mM $NaCl_2$.

To select peptide sequences from the mutant derived library for chemical synthesis we used the same criteria for the original peptide selection including a Higher Boman index (>2.3), the computed potential protein-protein interaction for a given amino-acids sequence, and a predicted instability index below 50. One hundred sixty mutant peptides (MPs) were selected for synthesis and 123 MPs were tested in triplicate against SpyCas9.

Example 11: Denaturing 15% Urea PAGE Secondary Assay

Figure 10A:
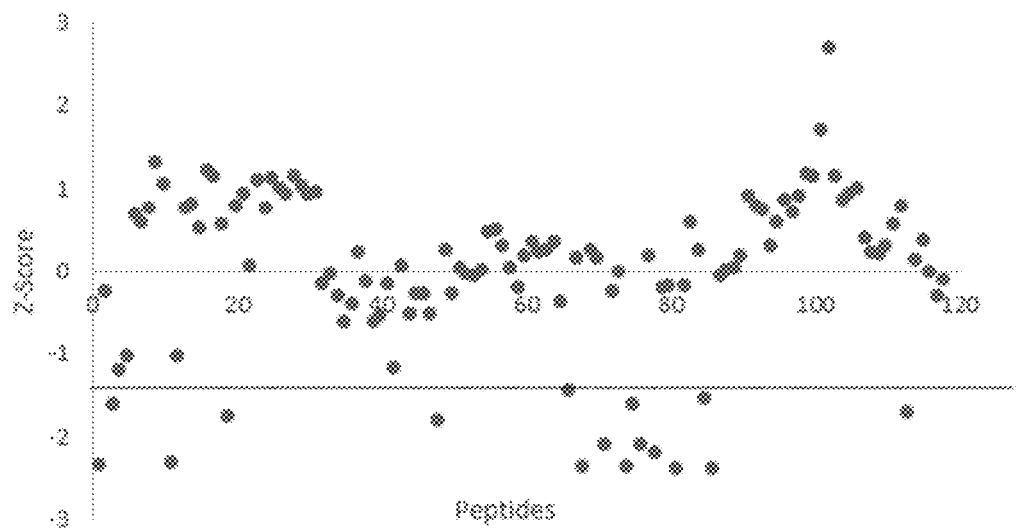
FIG. 10A is a statistical plot of Z-scores of synthesized mutant peptides based on fluorescence representing an affinity for Cas9.

The mutant peptides synthesized in Example 10 that had a Z-score of −1.5 or lower (FIG. 10A, calculated as disclosed above in Example 6) were selected for secondary screening via a 15% Urea PAGE assay to directly measure the inhibition of both the RuvC and HNH nuclease domains.

The 5' FAM target 50mer and 5' FAM nontarget 63mer oligonucleotides were purified by denaturing PAGE and annealed at 10 μM in 20 mM Tri-HCl (pH8.0) and 100 mM $NaCl_2$. Reactions were performed as above (Example 6), except that the dual FAM-labeled substrates were used. After 1 hour, the reactions were quenched by the addition of one volume of 2× TBE UREA (Thermo Fisher) loading buffer and were heated to 95° C. for 10 min to denature the substrate strands and analyzed by denaturing 8 M urea 15% polyacrylamide gel (Thermo Fisher). The gels were imaged for FAM fluorescence, and Imag J was used to analyze the intensity of the intact and cut bands for ratiometric quantitation.

Figure 10B:
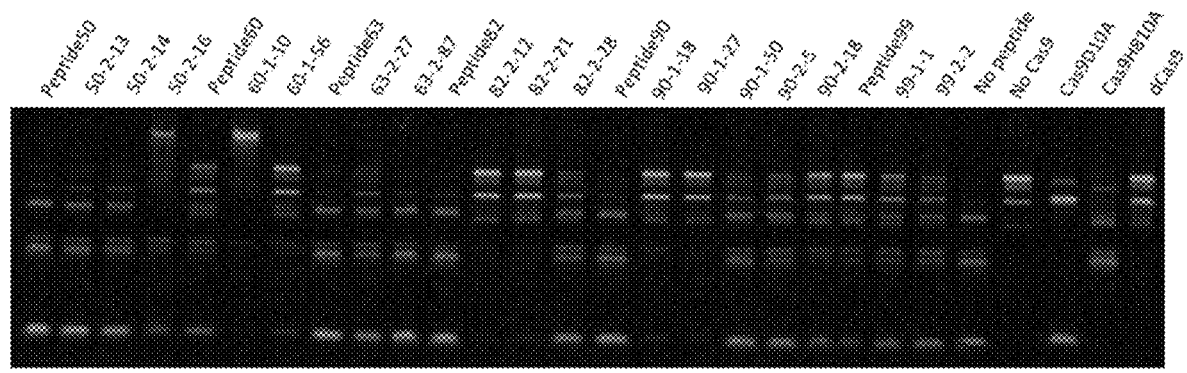
FIG. 10B is a photo showing secondary screening of mutant peptide inhibition by cleaved dual FAM-labeled substrate on denatured gel (15% urea PAGE).

17 hits were identified that reduced fluorescence and substrate cleavage in the Cas9 cleavage reaction (visualized by Gel) at 200 μM (FIG. 10B).

Example 12: Peptide Profiling Against SpyCas9, SauCas9, and CjeCas9

For the 11 original peptides reactions (10 μL) were set up in Cas9 reaction buffer [20 mM Tris-HCl, pH 7.5, 100 mM NaCl, 5 mM $MgCl_2$, 0.1 mM EDTA] containing 50 nM annealed DNA substrate, 1.5 μM sgRNA, and 0.5 μM Cas9 in the wells of a black low volume 384-well plate. The reactions were incubated for 1 hour at ambient temperature with the indicated concentration of peptide; then, 10 μL, of 8 M Guanidine-HCl was added to quench the reaction. The plates were covered with an aluminum seal and incubated at 75° C. for 10 minutes and cooled down to RT before reading. Then to determine the efficacy and the spectrum of inhibition demonstrated by the 17 peptide hits derived from the mutant library, cleavage assays with varying concentrations of peptides and Spy, Sau or CjeCas9 RNP were performed and compared to its original peptide, from which the mutated sequence was originated.

Figure 11:
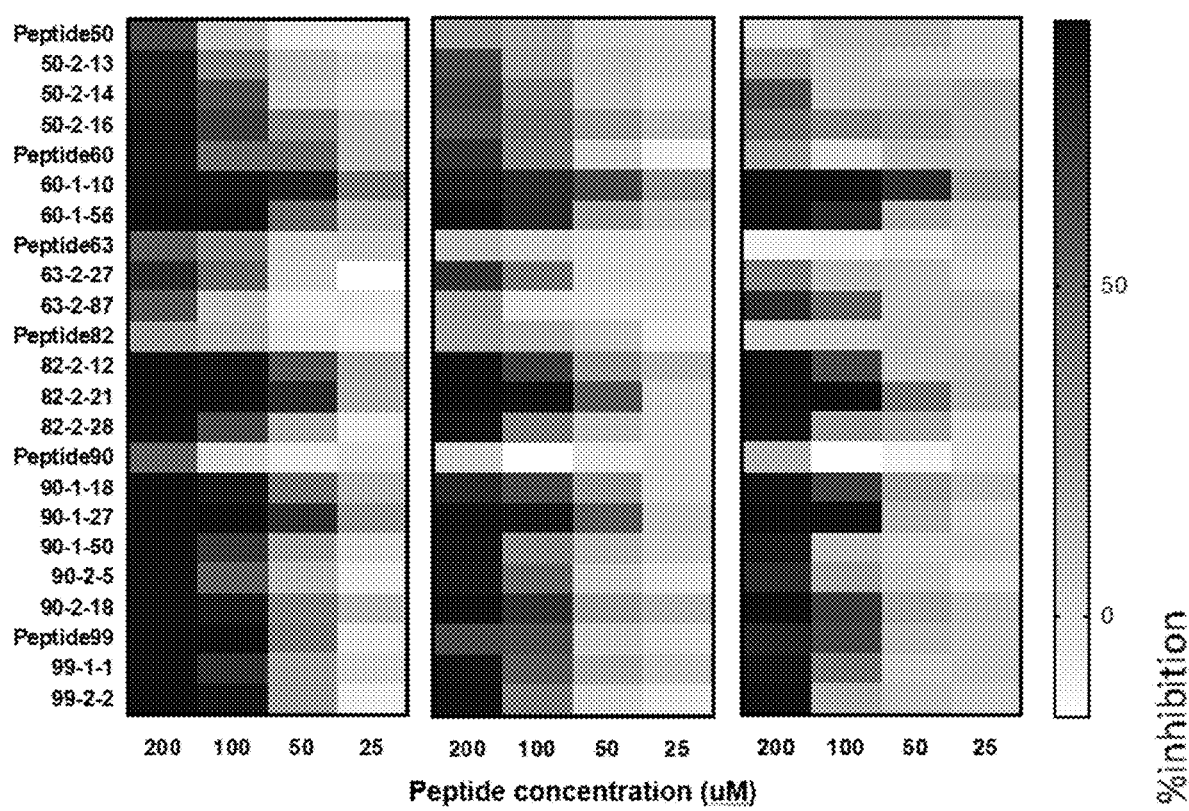
FIG. 11 is a heat map of several of the peptides and mutant analogs with the inhibition percentage for four concentrations.

FIG. 11 shows a heatmap of original and mutated peptides inhibition against Cas9 variants. The % inhibition was determined by subtracting normalized relative fluorescent value to Cas9 without peptides (% activity) from 100% cleavage activity of CjeCas9, SauCas9, SpyCas9 by FRET assay. Data are the average ±SD of eleven replicate wells from three technical replicates at the indicated concentration of peptides.

Figure 12A:
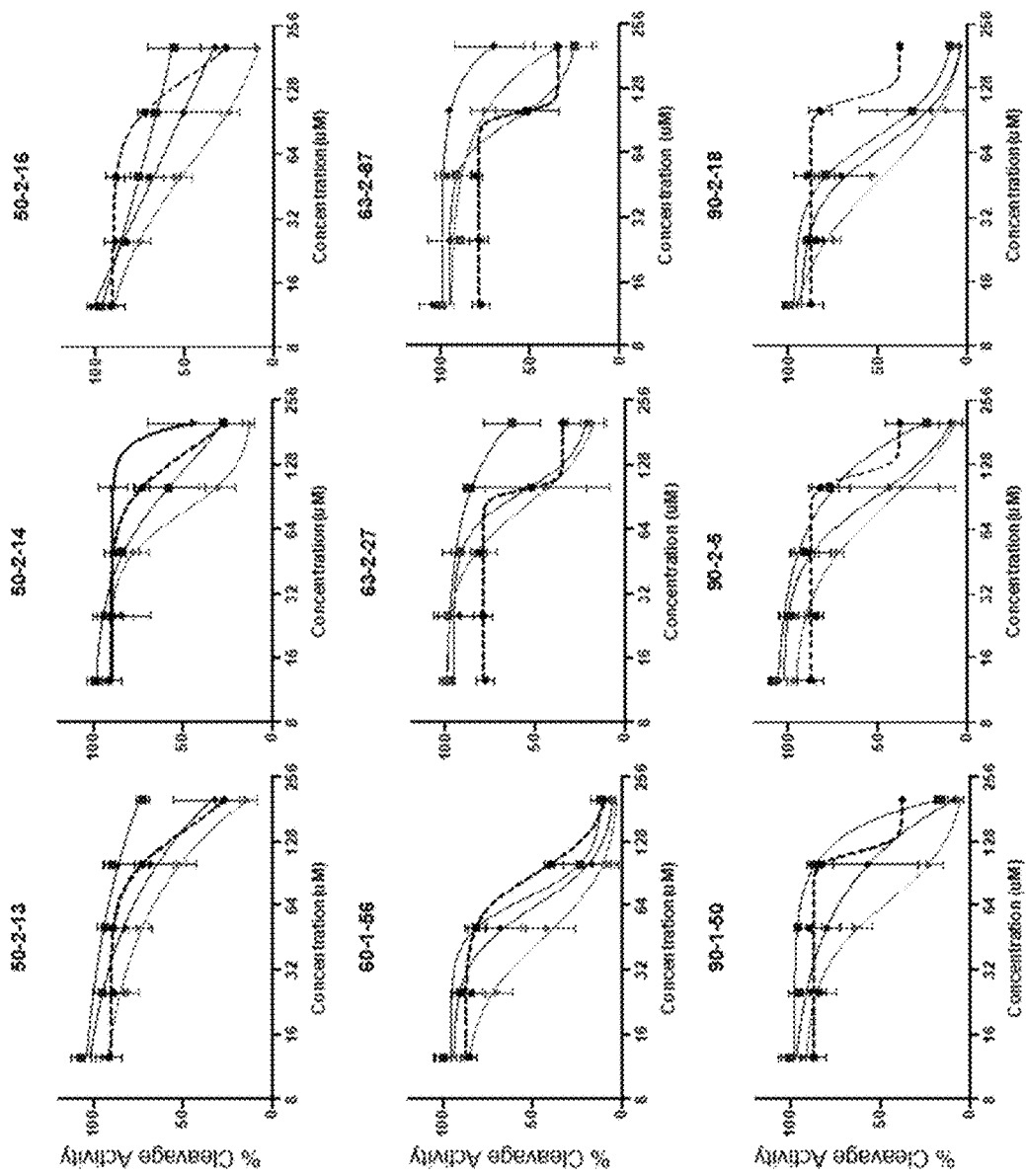
FIGS. 12A, 12B, and 12C are graphs showing mutated peptides inhibiting substrate cleavage in a peptide concentration-dependent manner in the comparison to original peptide.
Figure 12B:
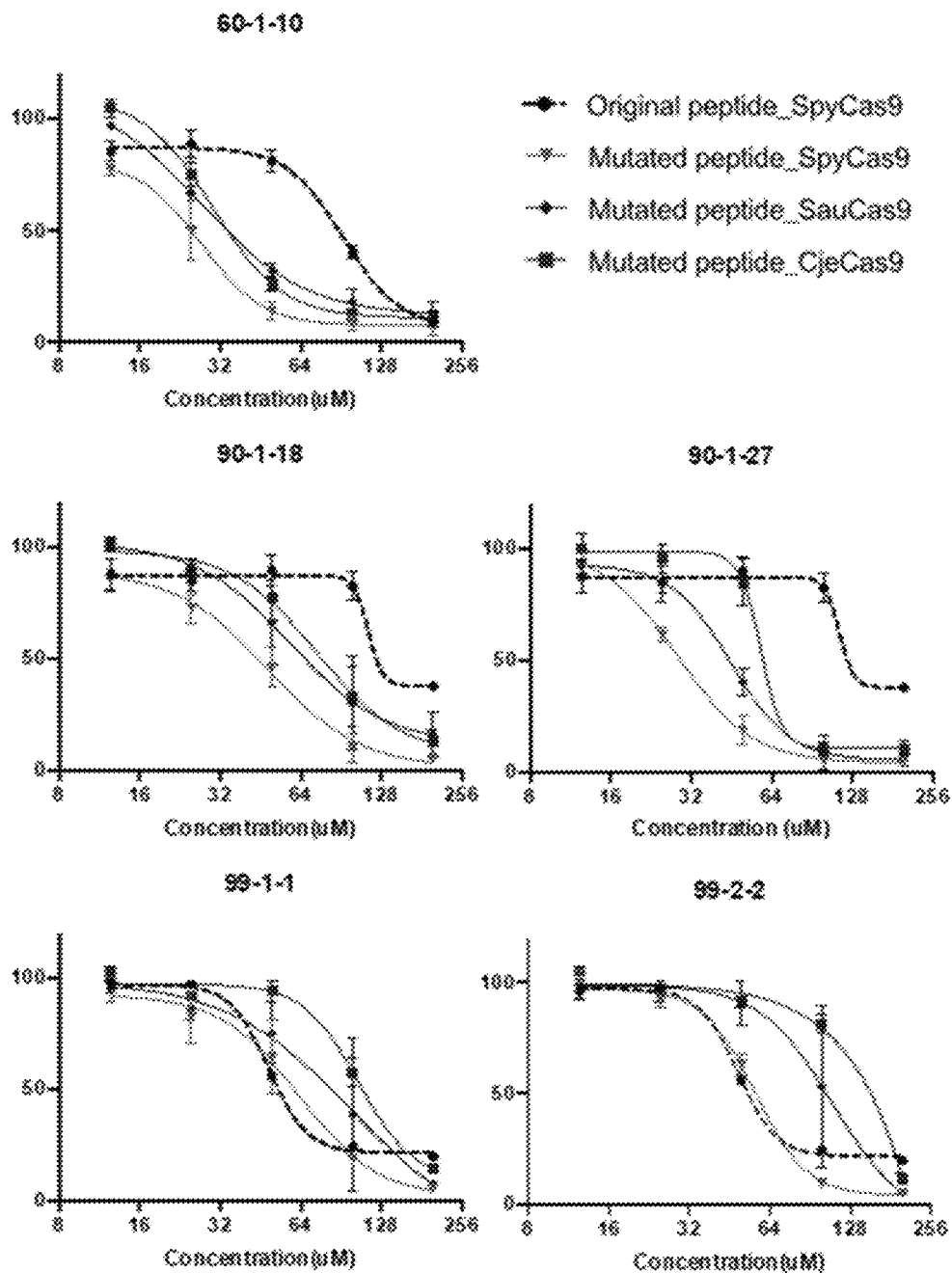
Figure 12C:
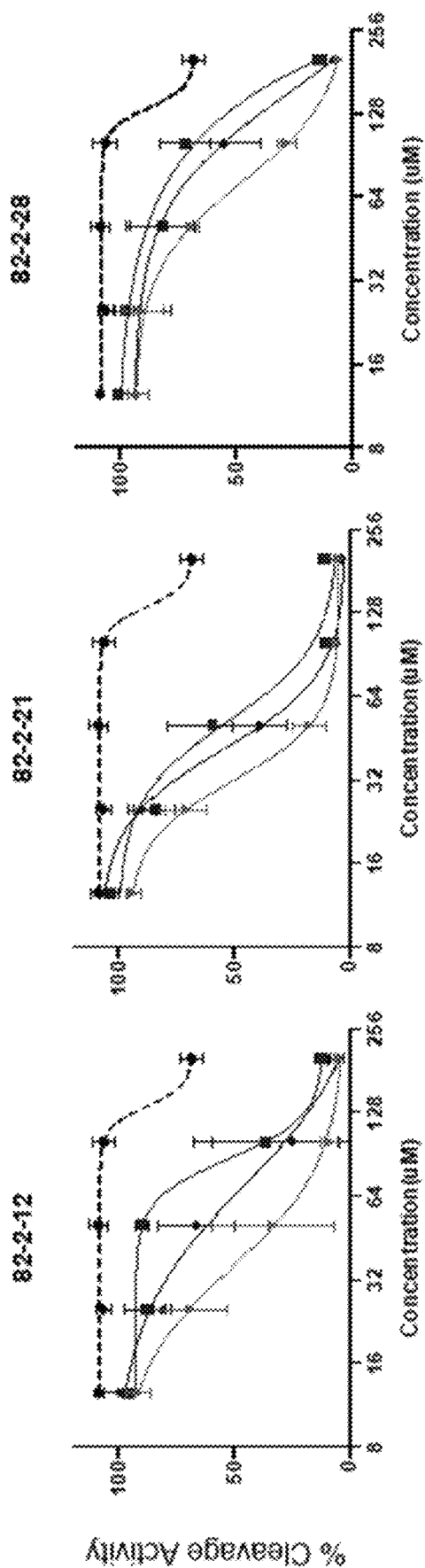

FIGS. 12A, 12B, and 12C show graphs of measurements and fitted curves of concentration dependent inhibition of mutated peptides against Cas9 variants. The inhibition was measured as relative fluorescent value to Cas9 without peptides (% activity) of CjeCas9 (line with squares), SauCas9 (line with diamonds), SpyCas9 (line with triangles) by FRET assay with the indicated concentration of peptides and compared to original peptides (line with circles). Data are the average ±SD of eleven replicate wells from three technical replicates.

Table 2 shows the $IC_{50S}$ determined by concentration curves of each new mutant peptide (MP) with each Cas9 variant and the IC50 of certain peptides identified from the original screen against SpyCas9.

TABLE 2

| | | SpyCas9 | | SauCas9 | | CjeCas9 | |
|---|---|---|---|---|---|---|---|
| Peptide | Sequence | IC50 (uM) | R^2 | IC50 (uM) | R^2 | IC50 (uM) | R^2 |
| Peptide50 | LYYRIMLSCPKYYPCELVGHTS | 144.6 | 0.97 | | | | |
| 50-2-13 | LNHRIMLSCPKYYLYELVGHTS | >200 | 0.96 | >200 | 0.73 | >200 | 0.87 |
| 50-2-14 | LYLRIMLSCPKNNPCGLVGHTS | 75.54 | 0.96 | 120.8 | 0.86 | >200 | 0.67 |
| 50-2-16 | LNHRIMLSCPKYYLYELVGHTS | 56.14 | 0.98 | >200 | 0.76 | >200 | 0.85 |
| Peptide60 | VCAFSADESLLIRRRHQRRRAG | 92.17 | 0.99 | | | | |
| 60-1-10 | VRVFSAYERLLIRRRRRRRRAG | 27.2 | 0.96 | 27.3 | 0.96 | 30.12 | 0.99 |
| 60-1-56 | VSAYSADESLLIRRRRRRRRAG | 44.6 | 0.96 | 62.93 | 0.94 | 69.16 | 0.95 |
| Peptide63 | LNVKIGNAHLTTIMSTMPLVLC | 97.94 | 0.97 | | | | |
| 63-2-27 | PNVKIGKAHLTTIMSTMPLIIC | 81.61 | 0.85 | 95.26 | 0.82 | >200 | 0.78 |
| 63-2-87 | LNVKIENAHLTTNLSTMPLVLC | >200 | 0.81 | >200 | 0.55 | 90.86 | 0.90 |
| Peptide82 | KERRRSLMQLSVKSNSLFLGGT | >200 | 0.95 | | | | |
| 82-2-12 | KERHRSLMRTTVKYYSLCLGGT | 35.32 | 0.90 | 68.97 | 0.85 | 87.05 | 0.88 |
| 82-2-21 | KERRRSMMQLSVKSYTLFLGGT | 31.77 | 0.99 | 40.9 | 0.98 | 51.79 | 0.94 |
| 82-2-28 | RERRRSLIQISVKSYPLFLGGT | 72.52 | 0.99 | 153.4 | 0.92 | >200 | 0.94 |

TABLE 2-continued

| Peptide | Sequence | SpyCas9 IC50(uM) | R^2 | SauCas9 IC50(uM) | R^2 | CjeCas9 IC50(uM) | R^2 |
|---|---|---|---|---|---|---|---|
| Peptide90 | DRSHKILLRYNGCHYRLLQRSL | 114.3 | 0.94 | | | | |
| 90-1-18 | DRSQKIFLRYNRCRYRLLQRGL | 48.41 | 0.97 | 58.39 | 0.90 | 73.57 | 0.95 |
| 90-1-27 | NRSHKILLHYNGCHYRLFLRSL | 28.47 | 0.99 | 44.99 | 0.98 | 58.32 | 0.98 |
| 90-3-50 | DGSLKILLRYNGCHYRLLQRSL | 65.48 | 0.97 | >200 | 0.88 | >200 | 0.98 |
| 90-2-5 | DRSHKILLRHSGCLYRFLQRYL | 86.46 | 0.89 | 91.33 | 0.90 | >200 | 0.90 |
| 90-2-18 | DRSHKILLCYNGRNKRLLLRRL | 47.25 | 0.97 | 68.23 | 0.90 | 74.93 | 0.90 |
| Peptide99 | -----RRSHIAWLLAMSLTWYS | 48.48 | 1.00 | | | | |
| 99-1-1 | GDPNSRRSHIARLLAMSLTWYS | 63.16 | 0.95 | 99.35 | 0.85 | 104.9 | |
| 99-2-2 | RDPNSRRSHIARLLAMSLTWYS | 56.17 | 0.99 | 109.6 | 0.87 | >200 | 0.98 |

*Table 2 corresponds to SEQ ID NOS 1-23, respectively, in order of appearance

The mutant peptides (MPs) reduced cleavage-based fluorescence in a dose-dependent manner. All of the MPs drastically reduced SpyCas9 substrate cleavage at 200 μM with a greater than 88% decrease in fluorescence. Many MPs also reduced SauCas9 and CjeCas9 mediated cleavage at 200 μM with a greater than 80% reduction in fluorescence.

As seen in Table 2 and FIG. 12, nine out of 14 MPs reduced the $IC_{50}$ in comparison to the original peptide, with four of the nine showing species specificity and only reducing the IC50 for SpyCas9 by approximately 2-2.5×. Six MPs had a significant $IC_{50}$ reduction for all Cas9 variants: peptide 50-2-16 in comparison to Peptide 50, peptides 60-1-10 and 60-1-56 in comparison to Peptide 60, peptide 90-1-27 in comparison to Peptide 90, peptide 81-2-12 and peptide 81-2-21 in comparison to Peptide 81. Peptide 60-1-10 showed the most noticeable improvement in efficacy for all three Cas9 variants with an IC50 of 27.2, 27.3 and 30.1204 for Spy, Sau and CjeCas9 respectively in comparison to the IC50 of 92.17 μM for original Peptide 60.

In summary of the results, it was shown that the first Cas9-selective binding/inhibitory peptides were made and tested using a phage display assay to screen an in-house peptide library of $1\times10^8$ random 22mer peptides displayed on T7-phage for high affinity binding to Cas9. The top 200 peptides identified by phage display were screened for inhibitory activity using a HT FRET-based activity assay to measure Cas9 cleavage activity and 11 hits were validated by denaturing PAGE. Six peptides were identified with reproducible micromolar efficacy against Spy Cas9. Three of these peptides also reduced SauCas9 activity at 200 μM (Peptide 60, Peptide 90, and Peptide 91), Peptide 15 significantly reduced activity of CjeCas9 and SpyCas9 at 100 μM (P<0.01) and 200 μM (P<0.005), and Peptide 99 significantly reduced activity of all three Cas9 variants at 100 and 200 μM (P<0.005), in the HT FRET-based activity assay. It believed that these results represent the first synthesis and identification of broad-spectrum Cas9 inhibitors that work against SpyCas9, and CjeCas9 and/or SauCas9.

The binding assay revealed that original Peptides 60 and 99 blocked Cas9 activity by reducing binding of the RNP to the DNA substrate but Peptides 15, 90, 91, and 73, did not reduce substrate binding suggesting that they block cleavage through another mechanism.

When the peptides were expressed in mammalian cells, Peptides 15, 50, 60 and 90 reduced SpyCas9 activity by 20-35% in a cellular context, without cell toxicity, indicating their potential as therapeutic inhibitors for SpyCas9. However, the $IC_{50}$s for these peptides are in the 60-3000 micromolar concentration range. To improve the $IC_{50}$, error prone PCR was used to randomly mutate the top 11 peptide hits identified in the primary screen to develop a new peptide phage library. This library was re-screened against biotin-SpyCas9/gRNA and an additional 160 peptides were chemically synthesized and tested for cleavage inhibition using the HT-FRET activity assay and validated by PAGE.

By screening this new mutant library, peptides were identified with significantly reduced $IC_{50}$ concentrations in comparison to the original peptide. In addition, several additional peptides were made that were shown to have low micromolar efficiency against SpyCas9, SauCas9 and CjeCas9 variants. This is believed to the first anti-CRISPR peptides that inhibit SpyCas9, CjeCas9 and SauCas9.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used.

It is claimed:

1. An agent selected from the group consisting of: an amino acid sequence having at least 90% sequence identity to any one of SEQ ID NOs: 1, 3-10, and 12-28 and combinations thereof;
wherein the sequence identity is calculated over a full length of the amino acid sequence.

2. The agent of claim 1, wherein the amino acid sequence is identical to any of SEQ ID NOs: 1, 3-10, and 12-28.

3. The agent of claim 1, comprising a combination of two or more of the amino acid sequences having at least 90% sequence identity to any one of SEQ ID NOs: 1, 3-10, and 12-28.

4. The agent of claim 1, wherein the agent is a peptide selected from the peptides represented by SEQ ID NOs: 6, 13, and 17 and combinations thereof.

5. A composition comprising an amino acid sequence having at least 90% sequence identity to any one of SEQ ID NOs: 1, 3-10, and 12-28; and a pharmaceutically acceptable excipient;
wherein the sequence identity is calculated over a full length of the amino acid sequence.

6. The composition of claim 5, wherein the composition is formulated for oral delivery.

7. The composition of claim 5, further comprising a CRISPR Cas9 agent.

8. The composition of claim 7, wherein the CRISPR Cas9 agent is a SpyCas9, SauCas9, or CjeCas9 variant.

9. The composition of claim 5, wherein the amino acid sequence is a peptide selected from the peptides represented by SEQ ID NOs: 6, 13, and 17 and combinations thereof.

10. The composition of claim 5, wherein the pharmaceutically acceptable excipient is a lipid-coated nanoparticle.

11. The agent of claim 1, wherein the agent is an amino acid sequence having at least 90% sequence identity to SEQ ID NO: 6.

12. The agent of claim 1, wherein the agent is an amino acid sequence having at least 90% sequence identity to SEQ ID NO: 13.

13. The agent of claim 1, wherein the agent is an amino acid sequence having at least 90% sequence identity to SEQ ID NO: 17.

14. The agent of claim 1, wherein the agent is an amino acid sequence having at least 90% sequence identity to SEQ ID NO: 5.

15. The agent of claim 1, wherein the agent is an amino acid sequence having at least 90% sequence identity to SEQ ID NO: 7.

16. The agent of claim 1, wherein the agent is an amino acid sequence having at least 90% sequence identity to SEQ ID NO: 16.

17. The agent of claim 1, wherein the agent is an amino acid sequence having at least 90% sequence identity to SEQ ID NO: 22.

18. The agent of claim 1, wherein the agent is an amino acid sequence having at least 90% sequence identity to SEQ ID NO: 23.

* * * * *

SEQUENCE LISTING

<160> NUMBER OF SEQ ID NOS: 31

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Leu Tyr Tyr Arg Ile Met Leu Ser Cys Pro Lys Tyr Tyr Pro Cys Glu
1               5                   10                  15

Leu Val Gly His Thr Ser
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Leu Asn His Arg Ile Met Leu Ser Cys Pro Lys Tyr Tyr Leu Tyr Glu
1               5                   10                  15

Leu Val Gly His Thr Ser
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Leu Tyr Leu Arg Ile Met Leu Ser Cys Pro Lys Asn Asn Pro Cys Gly
1               5                   10                  15

Leu Val Gly His Thr Ser
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Leu Asn His Arg Ile Met Leu Ser Cys Pro Lys Tyr Tyr Leu Tyr Glu
1               5                   10                  15

Leu Val Gly His Thr Ser
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 5

Val Cys Ala Phe Ser Ala Asp Glu Ser Leu Leu Ile Arg Arg Arg His
1               5                   10                  15

Gln Arg Arg Arg Ala Gly
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Arg Val Phe Ser Ala Tyr Glu Arg Leu Leu Ile Arg Arg Arg Arg
1               5                   10                  15

Arg Arg Arg Arg Ala Gly
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ser Ala Tyr Ser Ala Asp Glu Ser Leu Leu Ile Arg Arg Arg Arg
1               5                   10                  15

Arg Arg Arg Arg Ala Gly
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Asn Val Lys Ile Gly Asn Ala His Leu Thr Thr Ile Met Ser Thr
1               5                   10                  15

Met Pro Leu Val Leu Cys
            20

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Asn Val Lys Ile Gly Lys Ala His Leu Thr Thr Ile Met Ser Thr
1               5                   10                  15

Met Pro Leu Ile Ile Cys
            20

<210> SEQ ID NO 10
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Asn Val Lys Ile Glu Asn Ala His Leu Thr Thr Asn Leu Ser Thr
1               5                   10                  15

Met Pro Leu Val Leu Cys
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Glu Arg Arg Arg Ser Leu Met Gln Leu Ser Val Lys Ser Asn Ser
1               5                   10                  15

Leu Phe Leu Gly Gly Thr
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Glu Arg His Arg Ser Leu Met Arg Thr Thr Val Lys Tyr Tyr Ser
1               5                   10                  15

Leu Cys Leu Gly Gly Thr
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Glu Arg Arg Arg Ser Met Met Gln Leu Ser Val Lys Ser Tyr Thr
1               5                   10                  15

Leu Phe Leu Gly Gly Thr
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Glu Arg Arg Arg Ser Leu Ile Gln Ile Ser Val Lys Ser Tyr Pro
1               5                   10                  15
```

Leu Phe Leu Gly Gly Thr
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser His Lys Ile Leu Leu Arg Tyr Asn Gly Cys His Tyr Arg
1               5                   10                  15

Leu Leu Gln Arg Ser Leu
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Ser Gln Lys Ile Phe Leu Arg Tyr Asn Arg Cys Arg Tyr Arg
1               5                   10                  15

Leu Leu Gln Arg Gly Leu
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Arg Ser His Lys Ile Leu Leu His Tyr Asn Gly Cys His Tyr Arg
1               5                   10                  15

Leu Phe Leu Arg Ser Leu
            20

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Gly Ser Leu Lys Ile Leu Leu Arg Tyr Asn Gly Cys His Tyr Arg
1               5                   10                  15

Leu Leu Gln Arg Ser Leu
            20

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 19

Asp Arg Ser His Lys Ile Leu Leu Arg His Ser Gly Cys Leu Tyr Arg
1               5                   10                  15

Phe Leu Gln Arg Tyr Leu
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Arg Ser His Lys Ile Leu Leu Cys Tyr Asn Gly Arg Asn Lys Arg
1               5                   10                  15

Leu Leu Leu Arg Arg Leu
            20

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Ser His Ile Ala Trp Leu Leu Ala Met Ser Leu Thr Trp Tyr
1               5                   10                  15

Ser

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Asp Pro Asn Ser Arg Arg Ser His Ile Ala Arg Leu Leu Ala Met
1               5                   10                  15

Ser Leu Thr Trp Tyr Ser
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asp Pro Asn Ser Arg Arg Ser His Ile Ala Arg Leu Leu Ala Met
1               5                   10                  15

Ser Leu Thr Trp Tyr Ser
            20

<210> SEQ ID NO 24
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Ala Gly Phe Arg Arg Glu Trp Phe Asn Gln Asn Thr Tyr Phe Glu
1               5                   10                  15

Asn Trp His Ala Asp Arg
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Leu Tyr His Gln Cys Phe Leu Ala Cys Leu Ile Asp Arg Gln Ser
1               5                   10                  15

Pro Arg Asn Val
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Arg Gln Ile Ser Asn Thr Ser Ile Val Met Gly Thr Thr Pro Ser
1               5                   10                  15

Ser Val Ala Val Cys Gly
            20

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Glu Ser Ile Arg Ser Tyr Phe Ala Met Thr Ile Arg Arg Asn His
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Tyr Asp Phe Tyr Arg Met Leu Ser His Phe Phe Leu Lys Gly Pro
1               5                   10                  15

Ser Arg
```

```
<210> SEQ ID NO 29
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(82)
<223> OTHER INFORMATION: a, c, t, g, unknown or other

<400> SEQUENCE: 29
ccgggatccg aattccnnnn nnnnnnnnnn nnnnnnnnnn nnnnnnnnnn nnnnnnnnnn      60
nnnnnnnnnn nnnnnnnnnn nntgaaagct tgcggccgc                            99

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aatgatacgg cgaccaccga gatctacact ctttccctac acgacgctct tccg            54

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caagcagaag acggcatacg agatattggc gtgactggag ttcagacgtg tgctcttccg      60
atc                                                                  63
```